(12) United States Patent
Iannotti

(10) Patent No.: US 12,193,775 B2
(45) Date of Patent: Jan. 14, 2025

(54) METHOD AND SYSTEM FOR REMOTE ROBOTIC CONTROL OF POSITIONING OF AN INSTRUMENT

(71) Applicant: JPI Consulting, Delray Beach, FL (US)

(72) Inventor: Joseph P. Iannotti, Delray Beach, FL (US)

(73) Assignee: JPI Consulting, Delray Beach, FL (US)

( * ) Notice: Subject to any disclaimer, the term of this patent is extended or adjusted under 35 U.S.C. 154(b) by 29 days.

(21) Appl. No.: 18/124,626

(22) Filed: Mar. 22, 2023

(65) Prior Publication Data

US 2023/0355333 A1 Nov. 9, 2023

Related U.S. Application Data

(60) Provisional application No. 63/339,042, filed on May 6, 2022.

(51) Int. Cl.
*A61B 34/35* (2016.01)
*A61B 34/10* (2016.01)
*A61B 34/30* (2016.01)

(52) U.S. Cl.
CPC .............. *A61B 34/35* (2016.02); *A61B 34/10* (2016.02); *A61B 2034/102* (2016.02); *A61B 2034/105* (2016.02); *A61B 2034/107* (2016.02); *A61B 2034/306* (2016.02)

(58) Field of Classification Search
CPC ... A61B 34/35; A61B 34/10; A61B 2034/102; A61B 2034/105; A61B 2034/107; A61B 2034/306; A61B 17/15; A61B 17/154; A61B 17/17; A61B 17/1659; A61B 17/1666; A61B 17/1746; A61B 17/1778; A61B 17/8897; A61B 2017/568; A61B 2034/2055; A61B 34/30; A61B 34/37; A61F 2/40; A61F 2/42; A61F 2/4609; A61F 2/32; A61F 2/38; A61F 2/4603;
(Continued)

(56) References Cited

U.S. PATENT DOCUMENTS

| 5,484,446 A | 1/1996 | Burke |
| 6,712,824 B2 | 3/2004 | Millard |
| 7,658,741 B2 | 2/2010 | Claypool |

(Continued)

FOREIGN PATENT DOCUMENTS

| WO | WO 2017/204832 A1 | 11/2017 |
| WO | WO 2018/013848 A1 | 1/2018 |
| WO | WO 2020/216934 | 10/2020 |

OTHER PUBLICATIONS

ISA/US International Search Report for International Application No. /PCT /US23/27969, filed Jul. 18, 2023 (4 pages).
(Continued)

*Primary Examiner* — Rachid Bendidi
(74) *Attorney, Agent, or Firm* — RowanTree Law Group, PLLC; Joseph W. Schmidt

(57) ABSTRACT

A method and system for controlling the configuration and/or orientation of an adjustable instrument using a remotely located robot. The remotely located robot is utilized in conjunction with replicated specifications of a three-dimensional (3D) dataset defining a spatial target within an object. The obtained information will be utilized to perform a step that will alter or manipulate the object using the adjusted instrument.

4 Claims, 23 Drawing Sheets

(58) Field of Classification Search
CPC ...... A61F 2002/4633; A61F 2002/4632; A61F 2002/4677
See application file for complete search history.

(56) References Cited

U.S. PATENT DOCUMENTS

| | | |
|---|---|---|
| 7,744,600 B2 | 6/2010 | Rangaiah et al. |
| 8,236,000 B2 | 8/2012 | Ammann |
| 8,403,934 B2 | 3/2013 | Angibaud |
| 9,386,998 B2 | 7/2016 | Wilkinson |
| 10,002,227 B2 | 6/2018 | Netravali |
| 10,940,021 B2 | 3/2021 | Mahfouz |
| 11,007,012 B2 | 5/2021 | Netravali |
| 11,026,700 B2 | 6/2021 | Shah |
| 2007/0100258 A1 | 5/2007 | Shoham |
| 2017/0004832 A1 | 1/2017 | Du et al. |
| 2017/0189131 A1* | 7/2017 | Weir ...................... B25J 9/1689 |
| 2019/0015167 A1 | 1/2019 | Draelos |
| 2019/0069961 A1* | 3/2019 | Smith ...................... A61B 5/06 |
| 2020/0093502 A1 | 3/2020 | Jones |
| 2022/0296302 A1* | 9/2022 | Bleunven .................. G06T 7/38 |

OTHER PUBLICATIONS

ISA/US International Written Opinion for International Application No. PCT/US23/27969, filed Jul. 18, 2023 (4 pages).

ISA/US International Search Report for corresponding International Application No. PCT/US23/20951, filed May 4, 2023 (10 pages).

ISA/US International Written Opinion for corresponding International Application No. PCT/US23/20951, filed May 4, 2023 (2 pages).

* cited by examiner

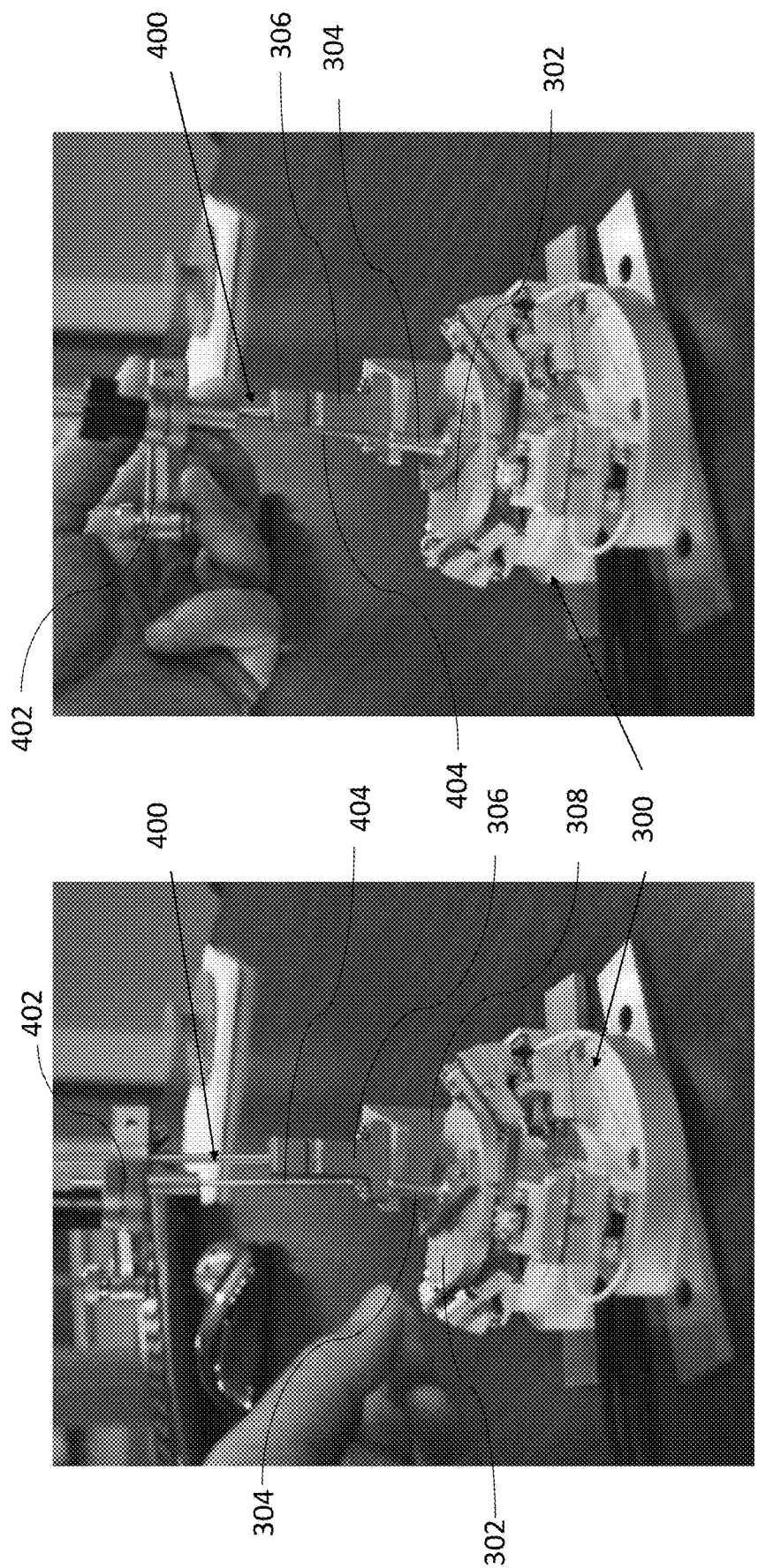

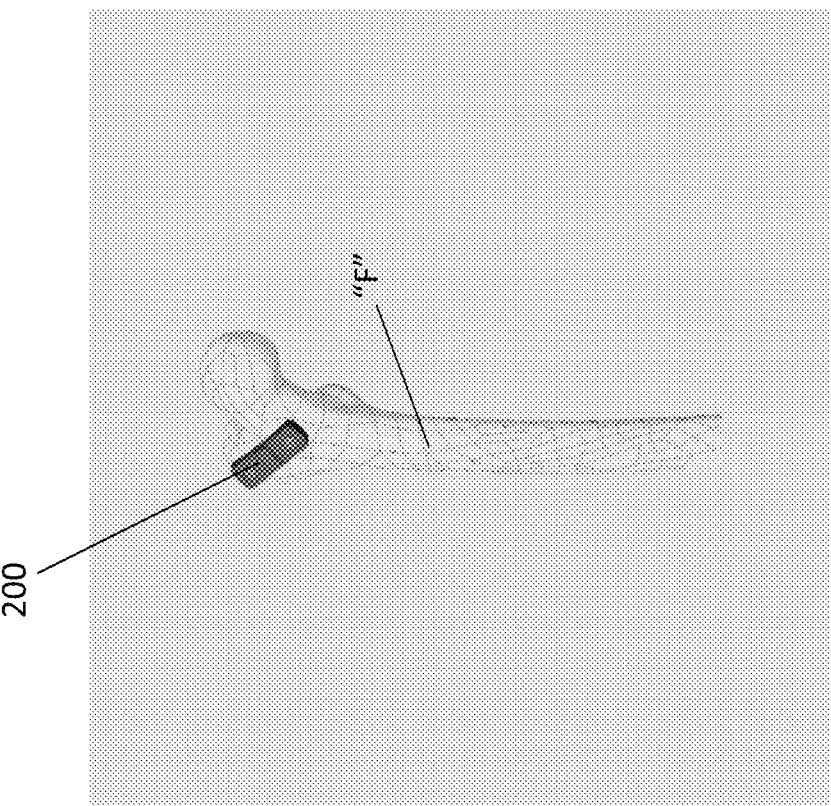
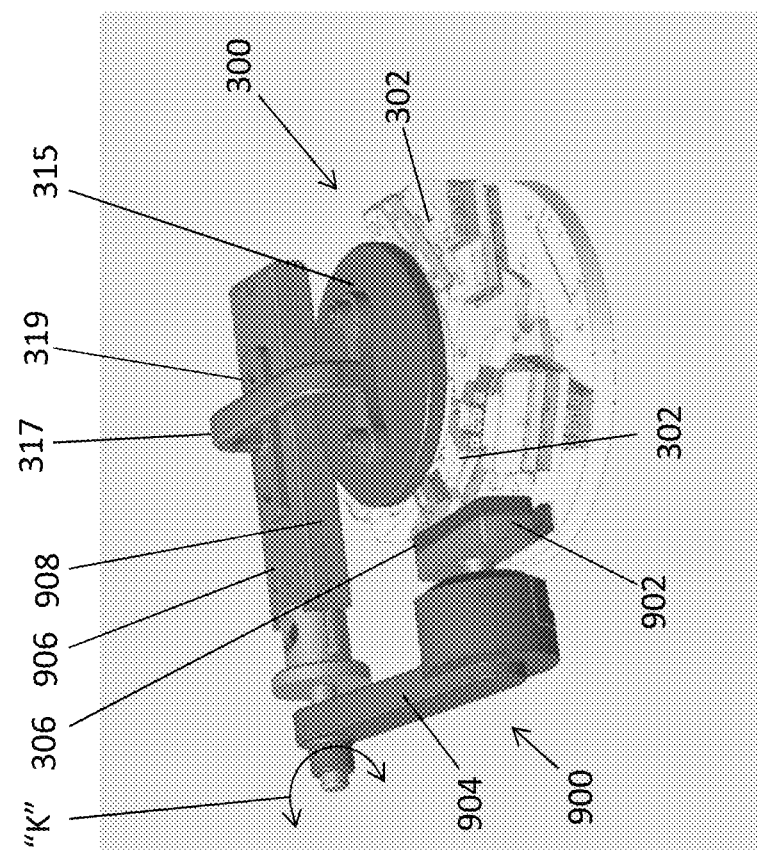
FIG. 19
FIG. 20A

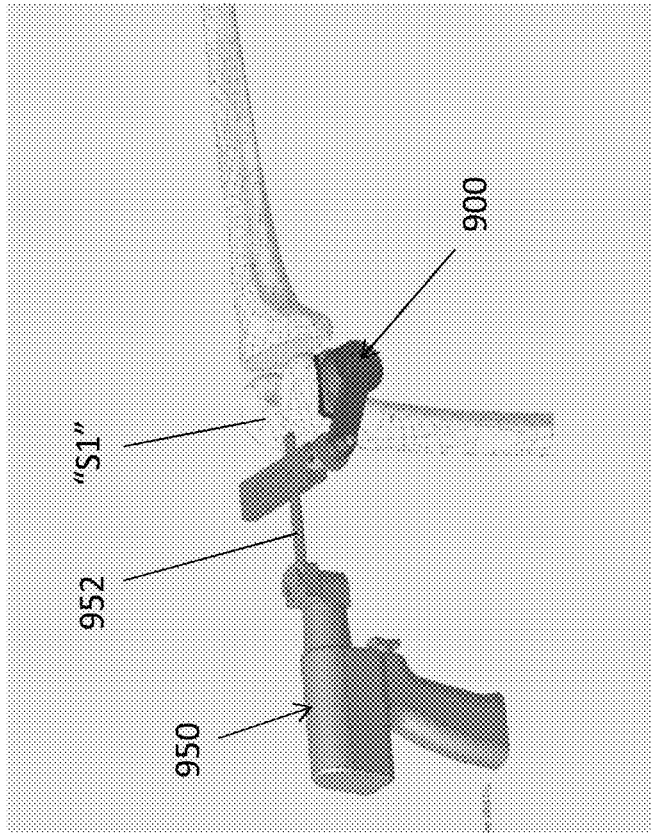
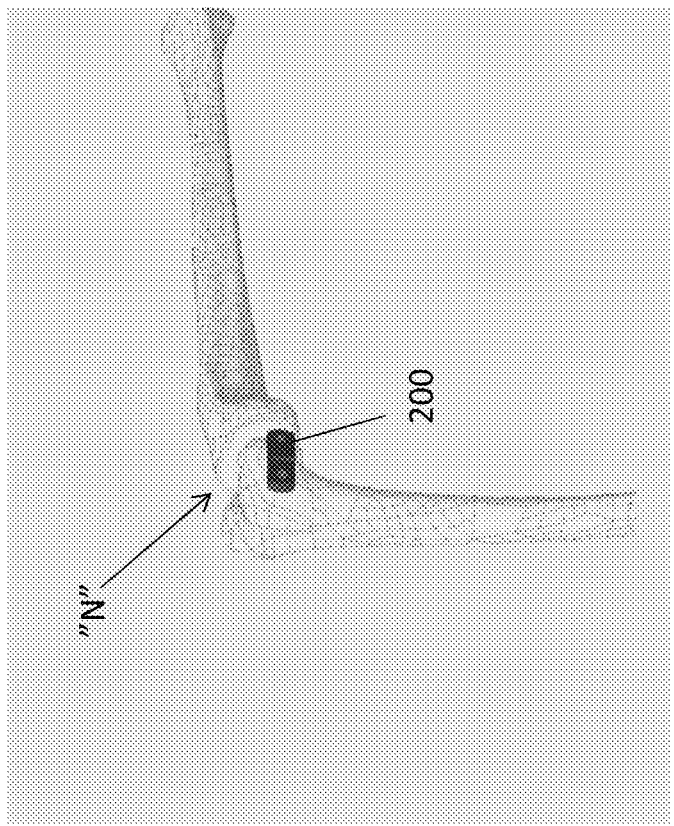
FIG. 22A
FIG. 22B

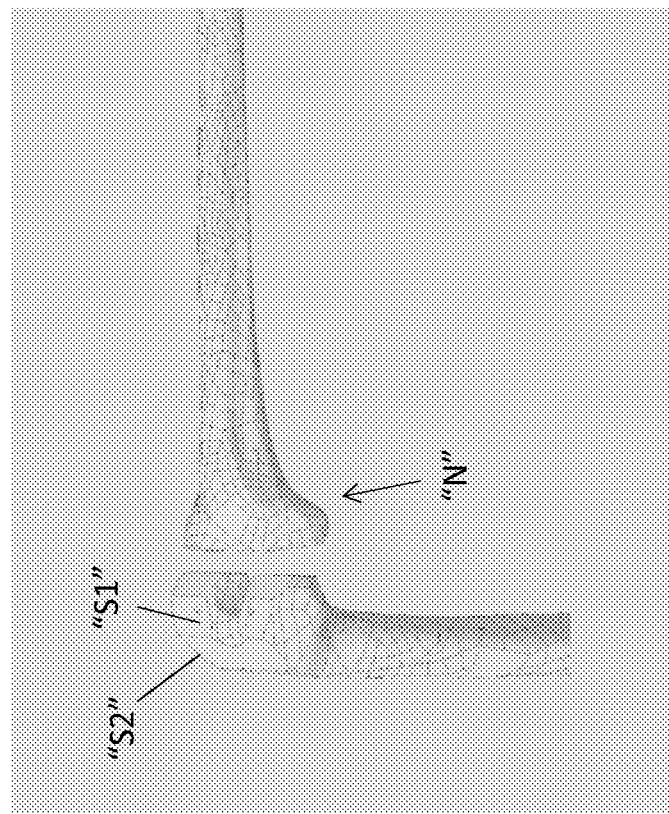
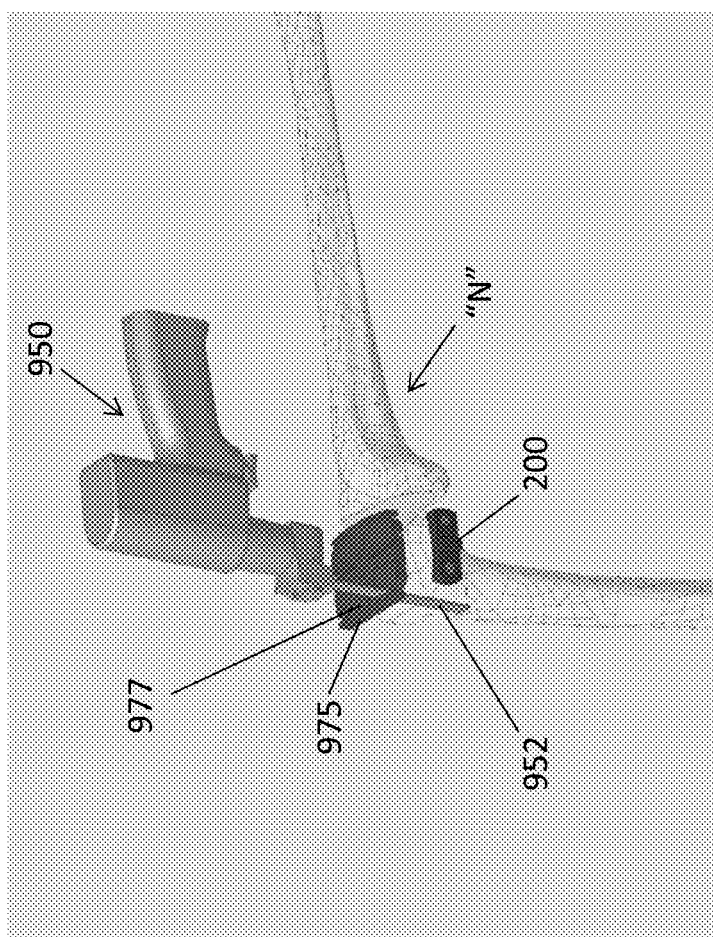
FIG. 22D
FIG. 22E

METHOD AND SYSTEM FOR REMOTE ROBOTIC CONTROL OF POSITIONING OF AN INSTRUMENT

CROSS-REFERENCE TO RELATED APPLICATION(S)

The present application claims priority to, and the benefit of, U.S. Application Provisional No: 63/339,042, filed May 6, 2022, the entire contents of which are incorporated by reference herein.

BACKGROUND

The present disclosure is directed to a method and system for controlling the configuration and/or orientation of an adjustable instrument using a remotely located robot. The remotely located robot is utilized in conjunction with replicated specifications of a three-dimensional (3D) dataset defining a spatial target within a site or object. The obtained information will be utilized to perform a step that will alter or manipulate the object using the adjusted instrument.

SUMMARY

In accordance with illustrative embodiments, 3D spatial data of the object is generated using pre-procedural and/or operative procedural 3D data of the object or structure obtained using laser or optical scanning, contact digitization, magnetic, ultrasound, x-ray or any method of imaging that defines the 3D shape of an object. A spatial target is defined within the structure or object. The spatial target includes a 3D plane or trajectory (e.g., an axis of trajectory) required to facilitate performance of one or more procedural steps on the object with one or more adjusted surgical instruments. The one or more procedural steps include, without limitation, altering, manipulating, moving, repairing, etc. the object with the adjusted instrument.

In illustrative embodiments, a remotely located robot adjusts a patient specific instrument (PSI) at a remote location to the specific configuration to replicate the spatial target in the object. Thereafter, the adjusted PSI is removed from the robot at the remote location and returned to the procedural site of the object and used to perform a step in the procedure. The surgical step is performed using the adjusted instrument either by an operator or using another robot or tool.

The remotely located robot is controlled by a navigation software that compares the 3D spatial target location to a reference mount fixed to the object at the procedural site. The software defines the 3D spatial target of the object to the object reference mount and compares this to a second reference mount of the same design that is fixed to the robot. The software defines and controls the robot to replicate the 3D target location of the object to the object reference mount. An adjustable instrument attached to the robot reference mount is adjusted to replicate the spatial target relationship of the robot and its reference mount. The adjustable instrument is locked into that specific position, then removed from the robot reference mount and placed onto the object reference mount and used by the operator to perform the 3D manipulation spatial target of the object.

The 3D digital data that defines the spatial target on, or in, the object can be obtained or generated before the object is manipulated (pre-procedural 3D data) and/or at the time the object is manipulated (procedural 3D data or intraoperative 3D data). In illustrative embodiments, the pre-procedural and procedural data can also be combined and registered to create a composite 3D dataset. This combined dataset incorporates the spatial target information defined in the pre-procedural 3D dataset with the procedural 3D dataset.

In general, the method, system and apparatus of the present disclosure have application in any surgical or manufacturing procedure in which an orientation and location of an instrument or tool may be adjusted via a remotely located robot. The robot is controlled using 3D data of the object and the spatial target that is obtained before and/or during the procedure.

The present disclosure has application across many technologies, including, but not limited to, several types of orthopedic procedures such as shoulder, knee, hip and ankle repair or any other arthroplasty or repair or other manipulation of the object during the procedure. The present disclosure also has application in dental, spinal or cranial surgical procedures. In addition, the present disclosure may be used in manufacturing processes to effectuate various steps involved in the manufacture or repair of an object using the manipulated instrument.

In accordance with one illustrative embodiment, a specific application is described for use in a shoulder replacement surgery for placement of a glenoid component which is achieved by placement and use of a guide pin. The location of the glenoid component (spatial target) in the glenoid (object) is based upon pre-procedural planning, using a pre-procedural 3D dataset (for example, a CT or MRI scan) obtained via any of the aforementioned means. In another illustrative embodiment, the 3D spatial dataset is obtained at the time of surgery or procedure and the spatial target within the object is defined. The spatial data including the spatial target is replicated. A patient specific instrument (PSI) is manipulated relative to the replicated data via a remotely located robot to correspond with the spatial target. The patient specific instrument (PSI) is removed from the remotely located robot and thereafter returned to the procedural site to perform the desired alteration of the object. In this embodiment, a preprocedural dataset is combined with procedural 3D spatial dataset for manipulation of the robot to a specific target location within the object that was define before the procedure. In the case of application of a glenoid guide pin, within that 3D dataset, the location and orientation of a guide pin (spatial target) is generated to simulate location or trajectory (e.g., axis of trajectory) of the guide pin within the glenoid bone (object). At the time of surgery, the glenoid bone is exposed and digitized, for example, mapped to define an operative procedural 3D dataset of the object. In this example, the pre-procedural 3D dataset (CT scan) and the operative procedural 3D dataset are registered to define a composite 3D dataset thereby bringing the spatial target (guide pin location and orientation) into the composite 3D dataset. In this manner, the spatial target (guide pin) is located within the object (real glenoid bone) defined by the procedural digitized dataset.

In one illustrative embodiment of the present invention, the patient specific instrument (PSI) is mounted to the glenoid by use of a surgical reference component (bone mount) firmly attached to the base of the coracoid at the time of the procedure. The surgical reference component may be a bone or tissue mount or any other reference element attachable to the surgical area of interest. The bone mount is digitized, for example, mapped and incorporated into the composite 3D dataset of the object. The bone mount thereafter serves as a fixed reference within the 3D dataset of the object. A second, same shaped reference instrument, in this case the coracoid bone mount, is fixed to the remote robot which is located at a location that is remote and not within the surgical or procedural field. The remote robot is controlled by the software and manipulated to replicate the spatial relationship between the spatial target in the object (glenoid guide pin) to the coracoid bone mount. The patient specific instrument attached to the robot reference instrument is manipulated to the spatial target location on the robot (guide pin location) and locked into that spatial relationship. This step replicates, within the PSI, the location and orientation of the spatial target (guide pin) in the object (glenoid bone) that is within the procedural area. The manipulated and locked instrument is moved back to the procedural site and placed onto the bone mount at the procedural site. The guide pin is inserted into the patient specific instrument and drilled into the bone thereby manipulating the object. This procedure has now replicated the location and trajectory of the guide pin in the glenoid bone defined by the pre procedural surgical plan and thereby the ultimate location of the glenoid component, for example, the guide pin.

In some applications, the excursions needed from the remotely located primary robot are insufficient to replicate a relationship of the reference instrument of the object to the spatial target of the object. In this circumstance, this invention prescribes placing the robot reference mount onto a second robot that is also controlled by the software. The second robot with its fixed reference mount moves a primary robot in relation to the reference instrument in order to allow the adjustable instrument to be adjusted within the excursion range of the primary robot.

Other advantages of the construction anchoring system will be appreciated from the following description. The descriptions include adjustable instruments for defining a trajectory or a plane for hip, knee and shoulder arthroplasty all using the same methods of digitization, registration, defining a spatial target, manipulation of the instrument using a remotely located robot and bringing the manipulated instrument back to the operative site to execute the desired change in the object.

BRIEF DESCRIPTION OF THE DRAWINGS

Various aspects and features of the present disclosure are described hereinbelow with references to the drawings, wherein:

FIGS. 10 and 11 are views illustrate manipulation of the PSI (400) to replicate the spatial target location (306) in relation to the reference mount after positioning of the robot (304);

FIG. 19 illustrates another embodiment of a PSI for use in establishing a spatial target as a plane in accordance with one or more exemplative embodiments of the present disclosure;

FIGS. 20A-20D illustrate use of the PSI of FIG. 19 with the remote robot in connection with performance of a total hip arthroplasty in accordance with one or more exemplative embodiments of the present disclosure;

FIGS. 22A-22E illustrate the use of the PSI of FIG. 19 in performing a total knee arthroplasty in accordance with one or more exemplative embodiments of the present disclosure;

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

Figure 1:
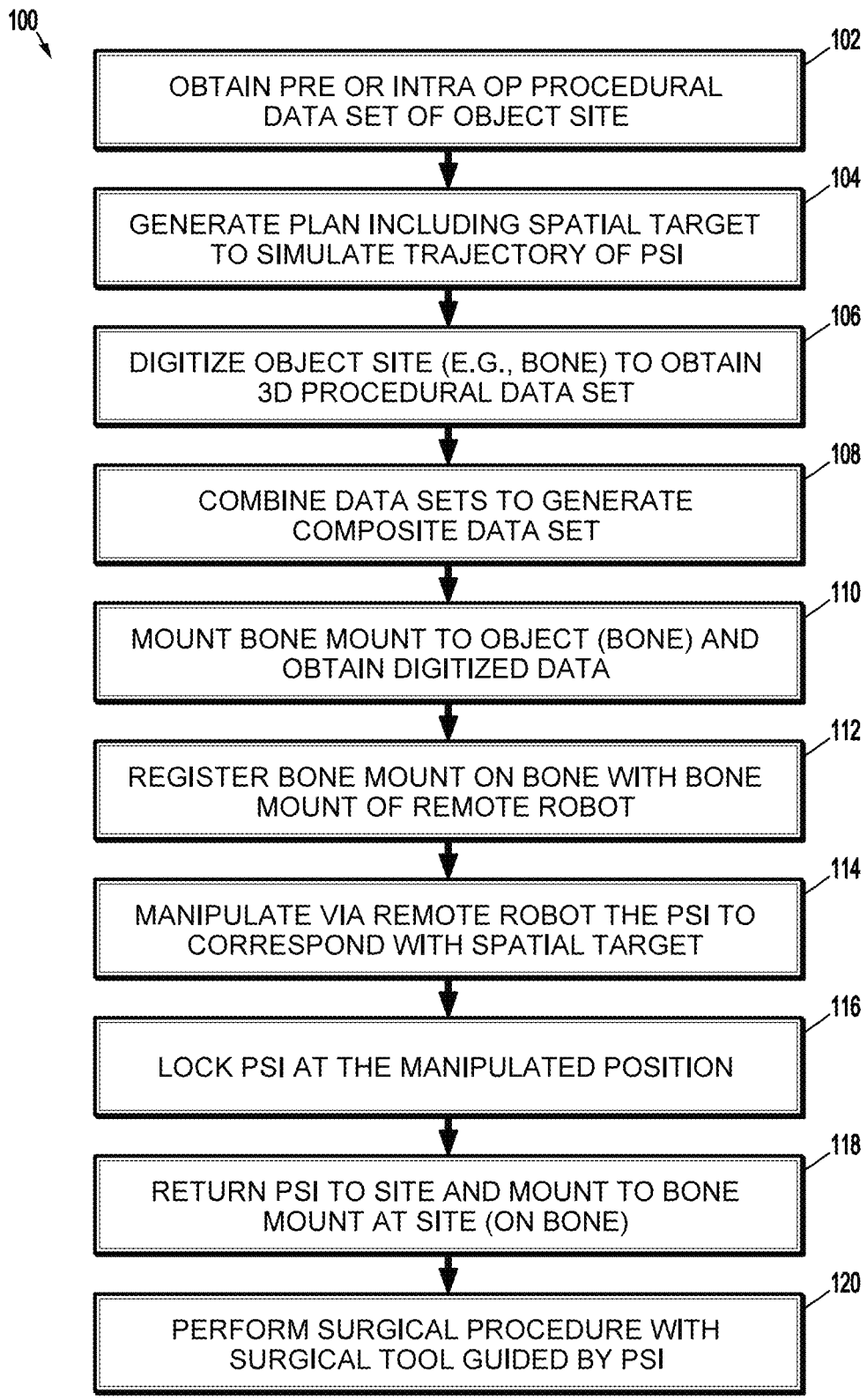
FIG. 1 is a flow chart illustrating a method of using the system in accordance with one or more exemplative embodiments of the present disclosure.

Referring now to the flow chart 100 of FIG. 1, there is illustrated an exemplary methodology and system in accordance with the principles of the present disclosure. The method and system will be described in the context of use thereof in connection with an orthopedic procedure, particularly, an arthroplasty procedure involving the glenoid structure of a patient. However, it is envisioned that the present disclosure may have various other applications including orthopedic hip, knee, spine procedures and also non-surgical processes including those involved in manufacturing or repair of goods, parts, equipment or machinery, etc.

The flow chart 100 of FIG. 1 includes a first process (STEP 102) for this specific example involving obtaining a digitized data set of the object site which, in this exemplative embodiment, is the glenoid structure of the shoulder. In illustrative embodiments, the digitized data set is obtained in a preprocedural stage or in an operative stage of the surgical procedure. In illustrative embodiments, the digitized data set (e.g., a 3D digitized dataset) is obtained using laser or optical scanning, contact digitization, magnetic, ultrasound, x-ray or any method of imaging that defines the 3D shape of an object at the object site. The location and/or orientation of a spatial target relative to the glenoid (object) is generated to simulate the location and direction of, for example, a patient specific instrument (PSI) to be used in association with the surgical procedure. The PSI may include a guide, guide pin or tube configured to introduce an implant or pin to be placed into the glenoid bone (object) as part of the surgical procedure. (STEP 104). In STEP 106, at the time of surgery, the object, i.e., the glenoid, is exposed and, through any of the aforementioned methodologies, digitized operative procedural data (e.g., a 3D digitized dataset) of the object is obtained. By way of example only, the operative procedural data may be obtained using a contact based digitizer such as the MicroScribe® 3D or a contact digitization and mapping system using an optical tracker for registration that is commonly used for surgical navigation. In another illustrate embodiment, imaging means, scanning, cameras for mapping and registration etc. are employed. In illustrative embodiments, the preprocedural and operative procedural data sets are combined to generate a composite digitized dataset. (STEP 108) In the orthopedics field, this composite digitized dataset enables a surgeon to plan an arthroplasty either pre-operatively or operative or other procedure by virtually placing models of tools, devices, guidewires, cutting blades, burring tools or other instruments to modify the object and place implants etc. into the 3D digitized dataset the patient's bone, in this example, the glenoid structure.

In STEP 110, the PSI is mounted to a surgical reference instrument (bone mount) relative to the glenoid at the time of the procedure. The PSI may have an adjustable terminal end. The bone mount or the PSI is digitized within the intraprocedural 3D dataset. Digitization may be effected via any of the aforementioned means. It is further envisioned that STEPS 106 and 110 may be combined in one scanning procedure. The 3D location of the spatial target is compared to the spatial location of the bone mount on the bone using navigation computer software. The bone mount on the robot and the bone mount on the bone are registered to one another and the spatial relation of the spatial target is defined to the registered location of the bone mount. (STEP 112)

The remotely located robot adjusts it position at a remote location to the position to replicate the spatial target in the object. (STEP 114). The remotely located robot is controlled by a navigation software executed by one or more processors that compares the 3D spatial location of the bone mount at the site of the object to the 3D spatial target within the object. The software defines and controls the robot to the defined location of the spatial target. The PSI attached to the bone mount of the remote robot is then manipulated to the position to the robot location of the guide pin and the PSI is locked into place. An alternative to this procedure would be to place the PSI on the bone mount of the remote robot in a loose condition and place the guide wire into the robot and the PSI. The robot would move the guide pin and PSI into the desired position and the PSI would be locked into this position. By either method, after the remote robot adjusts to the desired position the instrument, the components of the PSI are locked. (STEP 116) The PSI is returned to the site of the object and mounted relative to the bone mount in accordance with the spatial target at the precise location and orientation as effected by the remote robot. (STEP 118) Thereafter, the PSI is used to perform the surgical procedure in accordance with the defined spatial target. (STEP 120).

In other illustrative embodiments, the digitized preprocedural data is not obtained and the steps are conducted in accordance with the digitized operative data. For example, and without limitations, it is envisioned that the digitized operative data obtained in STEP 106 may be sufficient in performing other orthopedic procedures involving the hip, knee, etc. described hereinbelow.

In illustrative embodiments, one or more STEPS 102-120 of the methodology are performed by one or more processors coupled to memory.

Figure 2:
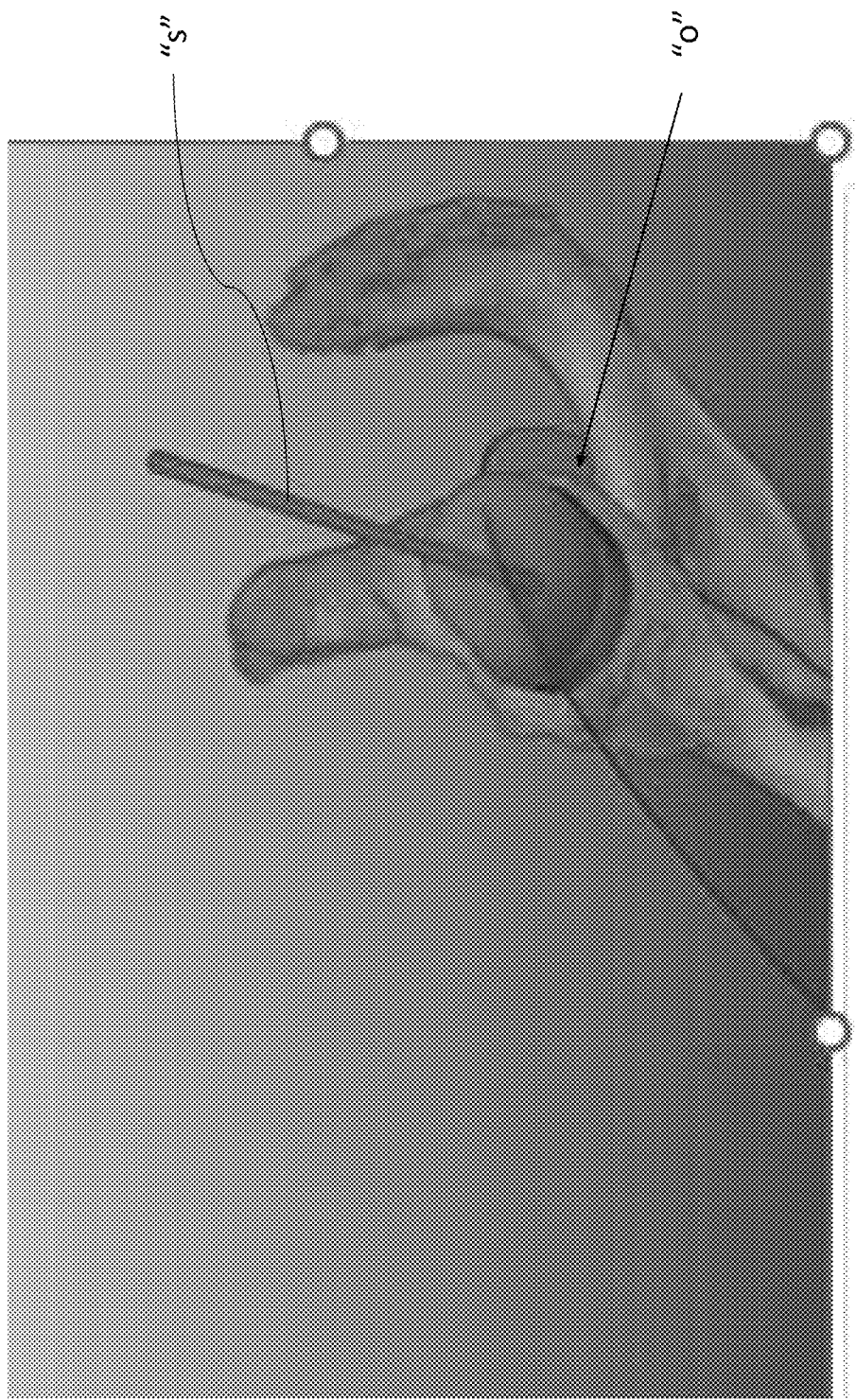
FIG. 2 is an image of a pre-operative plan. The view includes the glenoid bone and a glenoid implant with a spatial target (guide pin). The guide pin defines a spatial target in the glenoid. The spatial target defines the intended location and direction of a patient specific instrument (PSI) to be used in association with a surgical procedure in accordance with one or more exemplative embodiments of the present disclosure.

FIG. 2 illustrates a pre procedural 3D dataset for the example described herein where the surgical planned location of glenoid implant and the guide pin (spatial target) "s" is shown within the glenoid (object) in accordance with STEPS 102 and 104 of the flow chart 100 of FIG. 1

Figure 4:
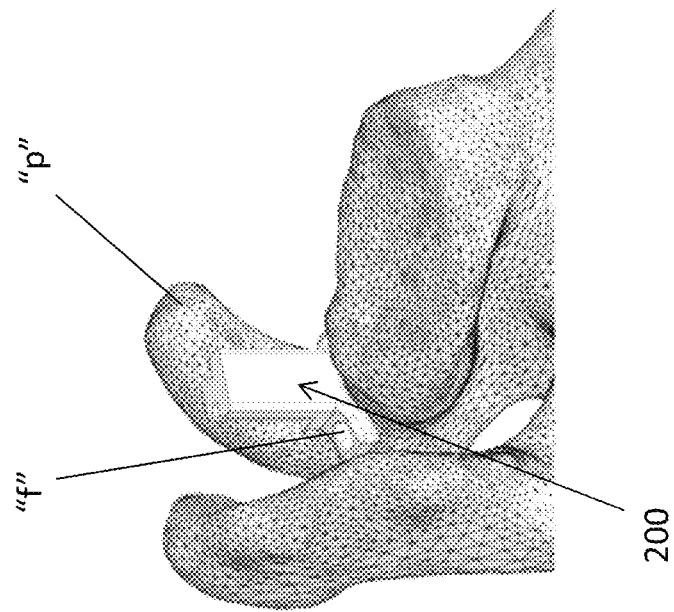
FIG. 4 is a view of the coracoid base with a reference instrument in the form of a bone mount (200) attached thereto in accordance with one or more exemplative embodiments of the present disclosure.
Figure 3:
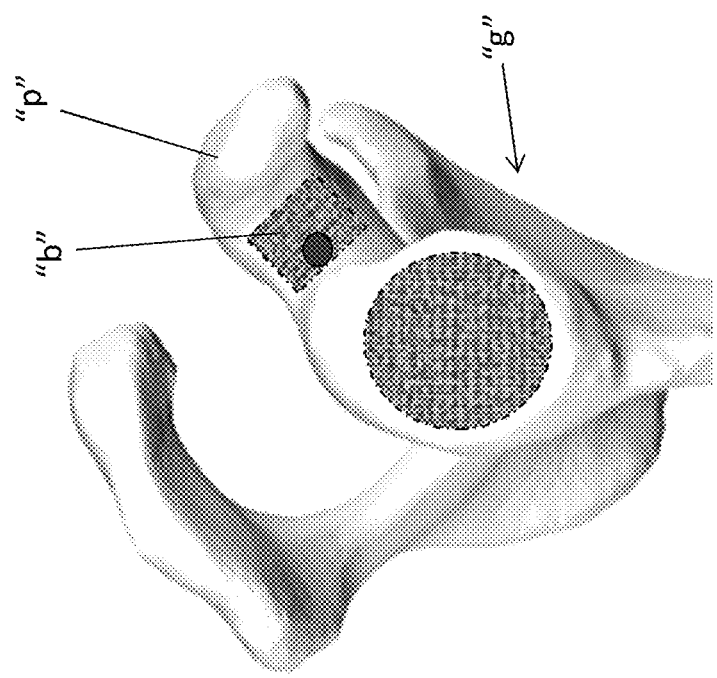
FIG. 3 is a view of the coracoid base (b) in accordance with one or more exemplative embodiments of the present disclosure.

FIG. 3 is a view of the glenoid bone structure "g" which may be subjected to, and incorporated in, STEP 106 of the flow chart of FIG. 1. The glenoid bone structure "g," the coracoid process "p" and the coracoid base "b" of the shoulder are depicted. In FIG. 4, a bone mount 200 is secured to the coracoid base "b." The bone mount 200 may be secured to the coracoid base "b" by one or more conventional orthopedic screws or fasteners "f" in association with STEP 110 of the flow chart 100. The bone mount 200 serves as a fixed surgical reference instrument for registration to an identical bone mount on the remote robot. It also serves as foundation to which the PSI is be mounted. It can also serve as a location to place and optical targeting device or surgical navigation. The bone mount 200 may be incorporated into the operative digitized data via the digitizer as described hereinabove or through other scanning processes associated with STEP 106 and/or STEP 110.

Figure 5:
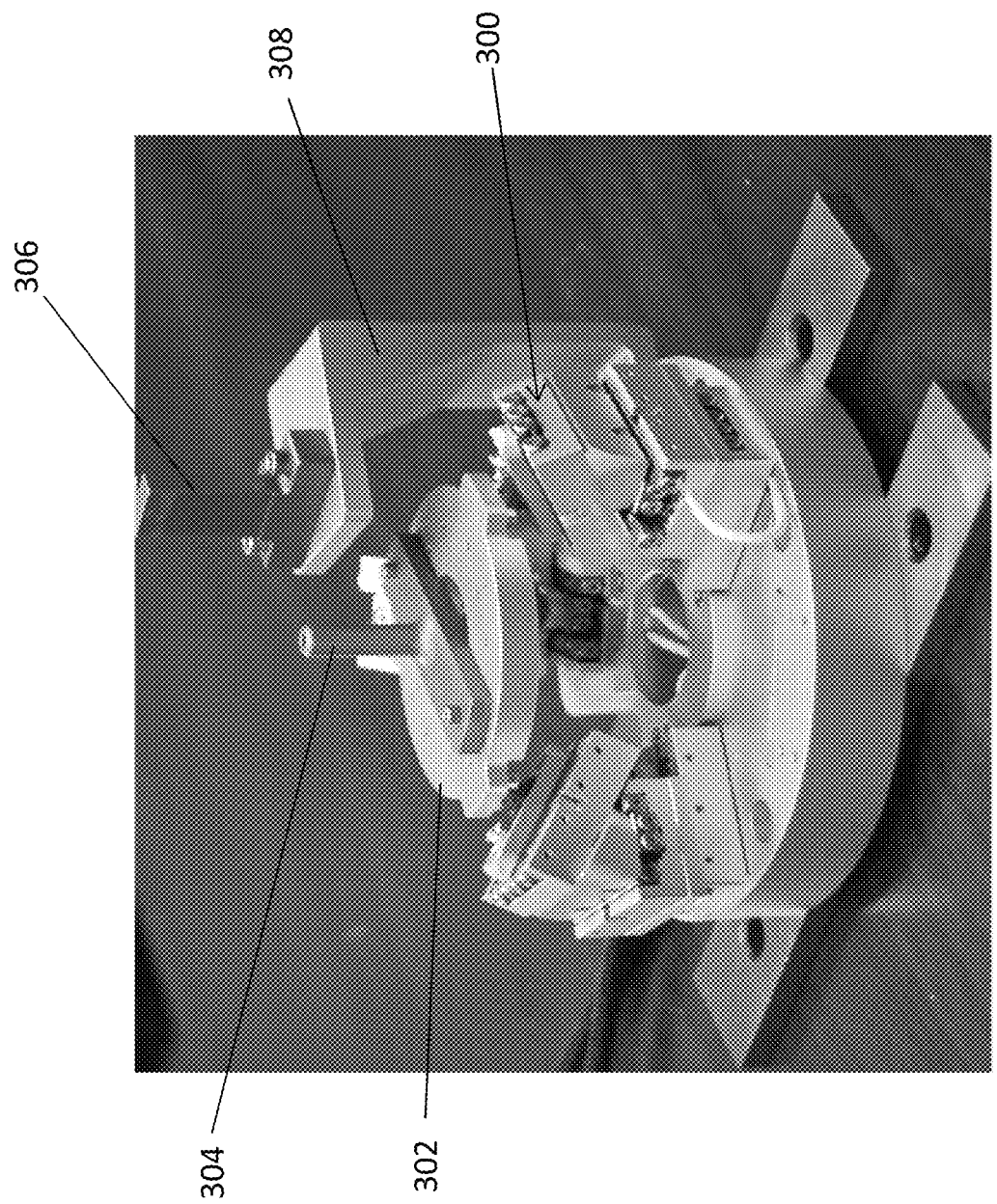
FIG. 5 is a view of a remotely located robot remote with a corresponding bone mount in accordance with one or more exemplative embodiments of the present disclosure.

FIG. 5 is a view of a remote robot 300. Other embodiments of a 6 degree of freedom robot that achieve the same desired goals are envisioned. The remote robot includes a multi-direction platform 302 which can manipulated through multiple axes of rotation including at least three axes and up to six (6) axes of rotation. Mounted to the platform 302 is a robot guide 304 which is generally aligned with the spatial target through manipulation of the platform in association with the flow chart of FIG. 1. A robot mount 306 is coupled to the remote robot 300 via robot arm 308. The robot mount 306 corresponds to the bone mount 200 on the glenoid bone structure "g." The bone mount 200 on the glenoid bone structure "g" and the robot mount 306 on the remote robot 300 are registered to one another as described in STEP 112 of the flow chart 100. The platform 302 and guide 304 of the remote robot 300 is controlled to move to replicate the spatial target "s" in the object relative to the bone mount 200 on the glenoid bone structure "g".

Figure 7:
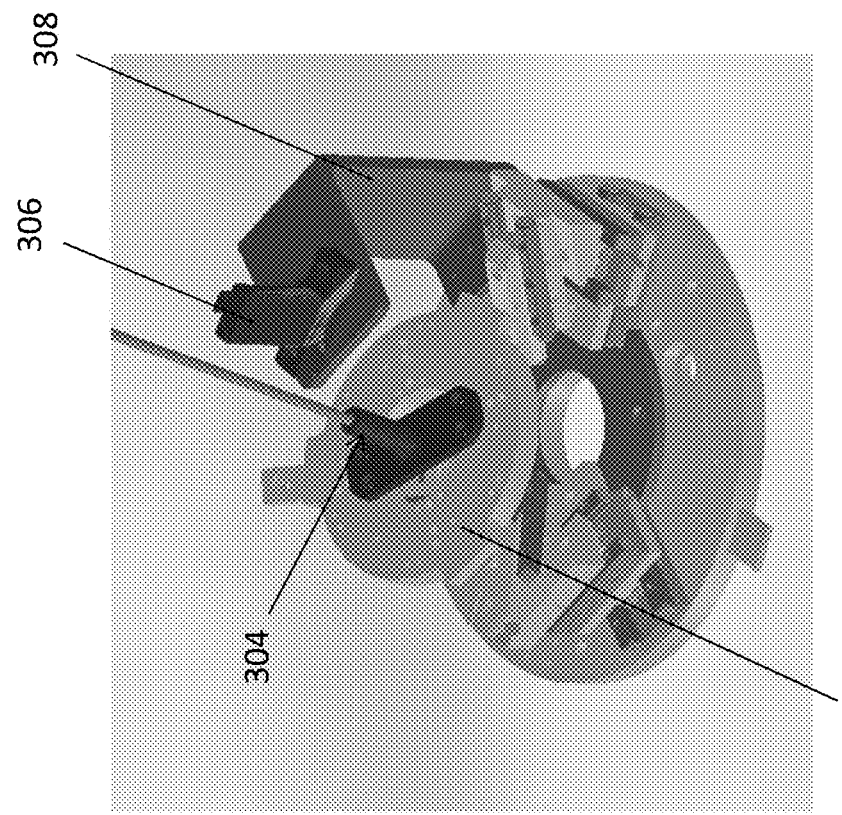
FIGS. 6 and 7 are views of the robot illustrating registration (overlapping) of the robot mount on the robot with the bone mount on the bone and the adjustment of the robot from its resting position (FIG. 6) to the spatial target location (FIG. 7) to align with the location of the guide pin in accordance with one or more exemplative embodiments of the present disclosure; These figures illustrate manipulation and movement of the robot platform to align the spatial target "s" with the guide 304 of the remote robot 300 in connection with STEP 114 of the flow chart 100.
Figure 6:
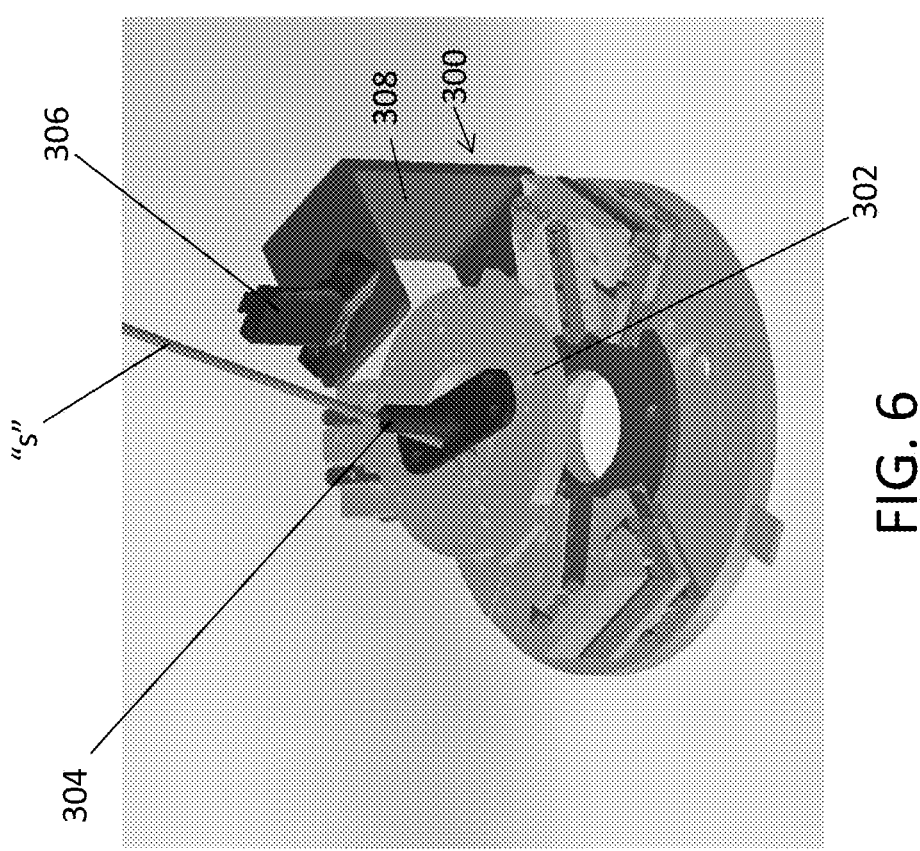

FIGS. 6 and 7 illustrate manipulation and movement of the robot platform 302 to align the spatial target "s" with the guide 304 of the remote robot 300 in connection with STEP 114 of the flow chart 100.

Figure 9:
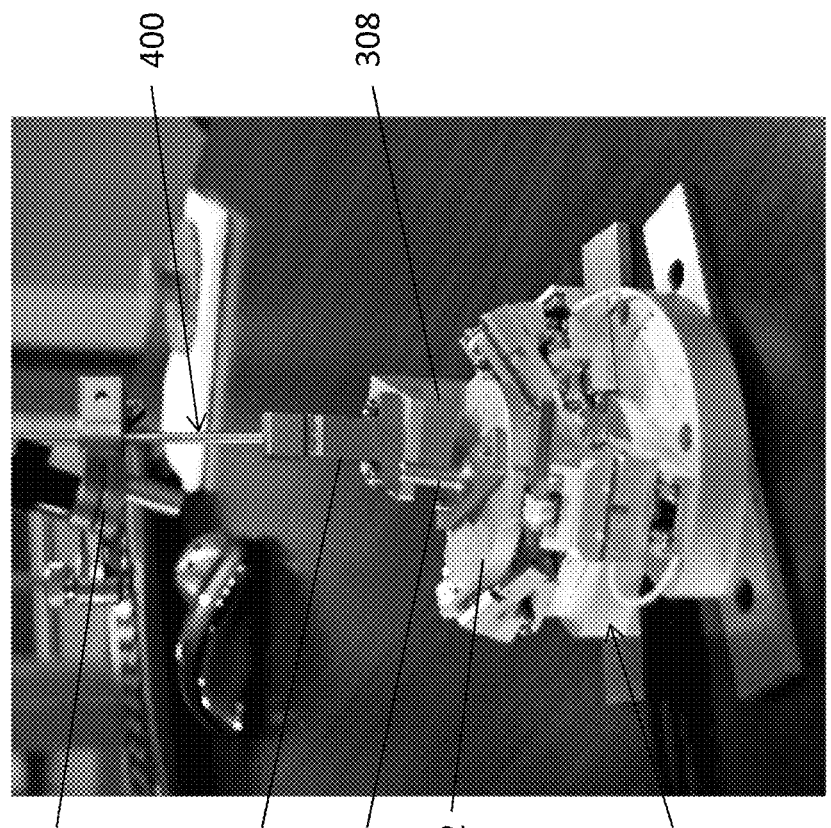
FIGS. 8 and 9 showing the robot in its pre-adjusted (FIG. 8) and after adjustment (FIG. 9) to the spatial target in relation to the robot bone mount 200 (FIG. 9)
Figure 8:
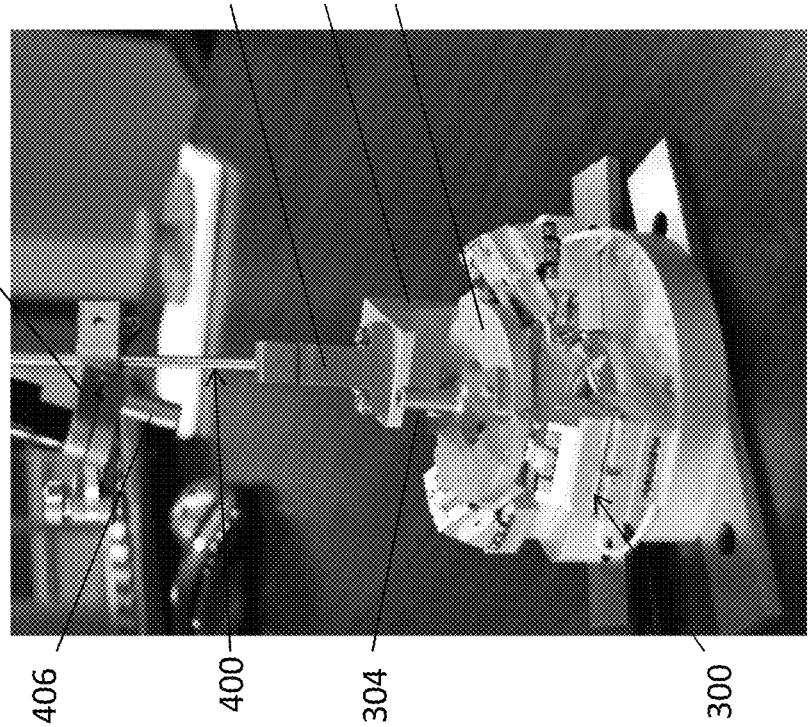

FIGS. 8-11 further illustrate manipulation and movement of the robot platform 302 of the robot relative to the spatial target "s" with one exemplative embodiment of a patient specific instrument (PSI) 400 mounted to the robot mount 306 of the remote robot 300. The PSI 400 may include one or more adjustable components forming an adjustable section 402 of the PSI 400. The components of the adjustable section 402 may be secured and released relative to each other to position a PSI guide 404 (FIGS. 10 and 11) at the desired orientation and arrangement corresponding to the orientation of the spatial target "s." FIGS. 8 and 9 illustrate the robot platform 302 moved to align the robot guide 304 with the spatial target "s." FIGS. 10 and 11 illustrate a sequence of introduction of the PSI guide 404 into the PSI 400 and insertion into the robot guide 304 of the remote robot 300. The PSI guide 404 may be a guide wire, guide tube, cannula or slot to define a plane etc. which, in illustrative embodiments, may be utilized, for example, in conjunction with a surgical tool such as a guide wire, reamer, drill saw blade or router tool etc. to perform a surgical procedure. In this position, the PSI guide 404 is aligned with the spatial target "s" due to the registration of the robot mount 306 with the bone mount 200 of the surgical site. Once positioned, the adjustable section 402 may be tightened. In other illustrative embodiments, the adjustable section 402 includes a guide tube section 406 through which the PSI guide 404 is positioned. Alignment of the PSI guide 404 with the spatial target "s" also aligns the guide tube section 406 with the spatial target "s." The guide tube section 406 may receive instrumentation to perform the surgical procedure in the absence of the PSI guide 404.

In other illustrative embodiments, the PSI 400, with the adjustable section 402 in a loose or non-tightened condition, may be placed on the robot mount 306. The PSI guide 404 may be positioned within the robot guide 304, the robot platform manipulated to position the PSI guide 404 in alignment with the spatial target "s" and thereafter the adjustable section tightened to secure the PSI guide tube 404 to correspond to the spatial target "s."

Figure 13:
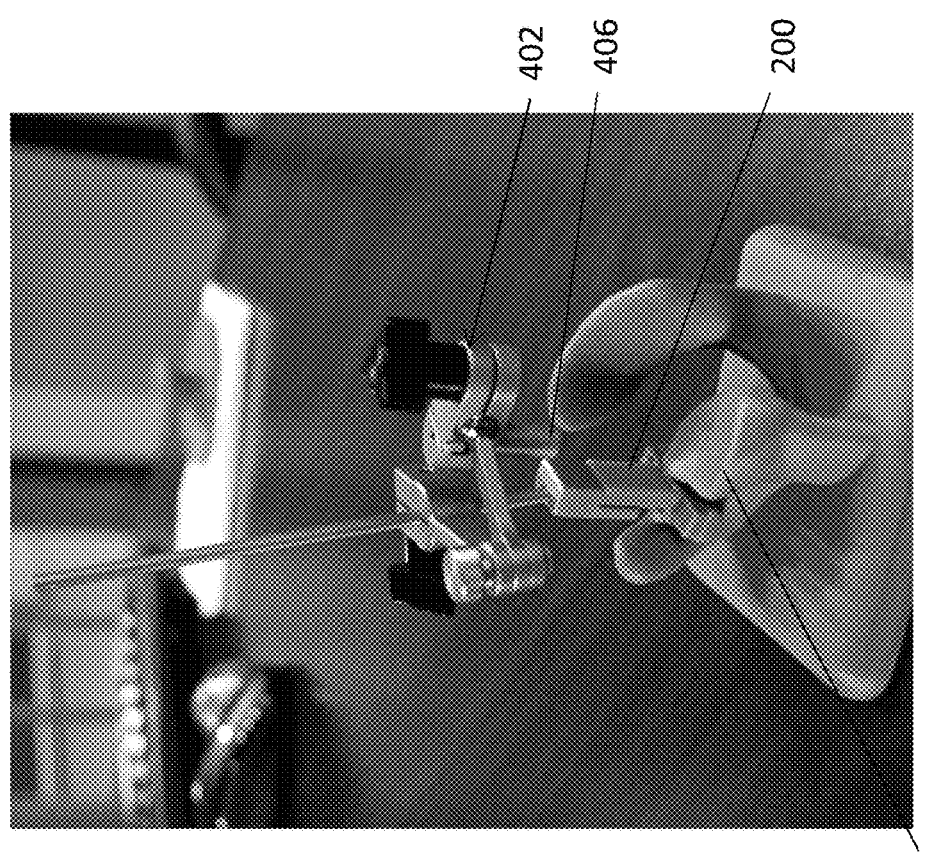
FIGS. 13 and 14 are views illustrating a sequence of insertion of a drill through a guide tube section of the PSI in accordance with one or more exemplative embodiments of the present disclosure.
Figure 12:
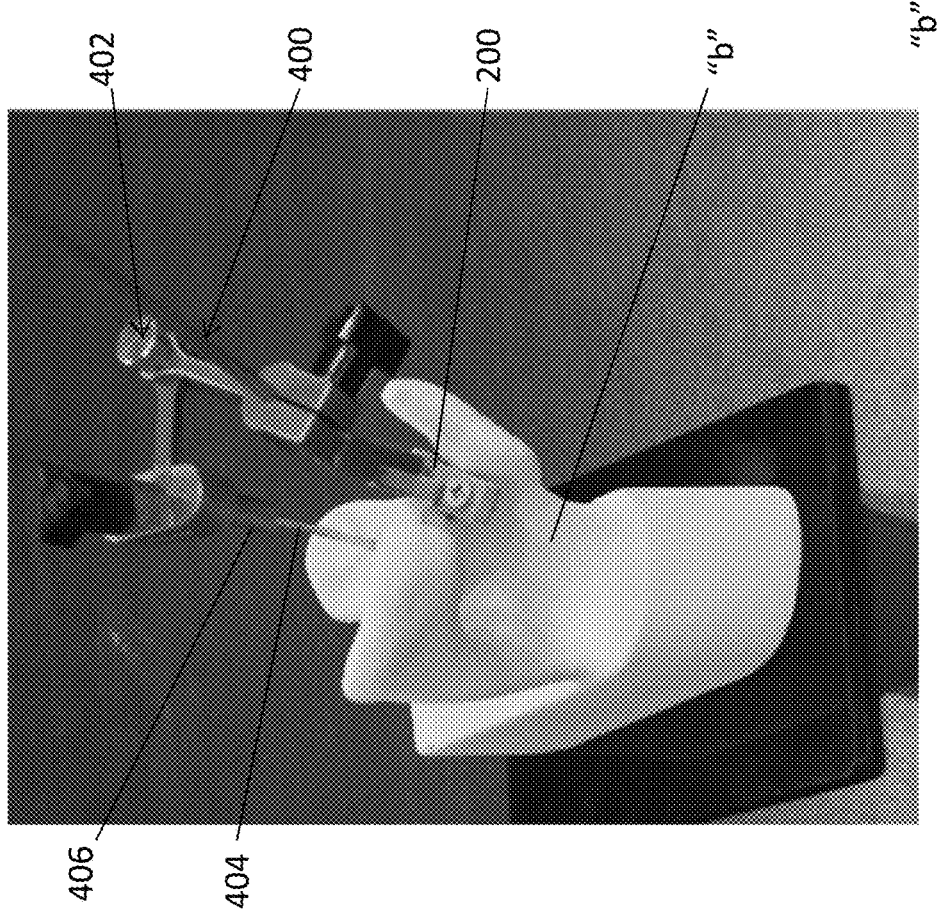
FIG. 12 is a view illustrating removal of the PSI removed from the bone mount of the remote robot and coupling it to the bone mount secured to coracoid base "b" of the shoulder in accordance with one or more exemplative embodiments of the present disclosure.
Figure 14:
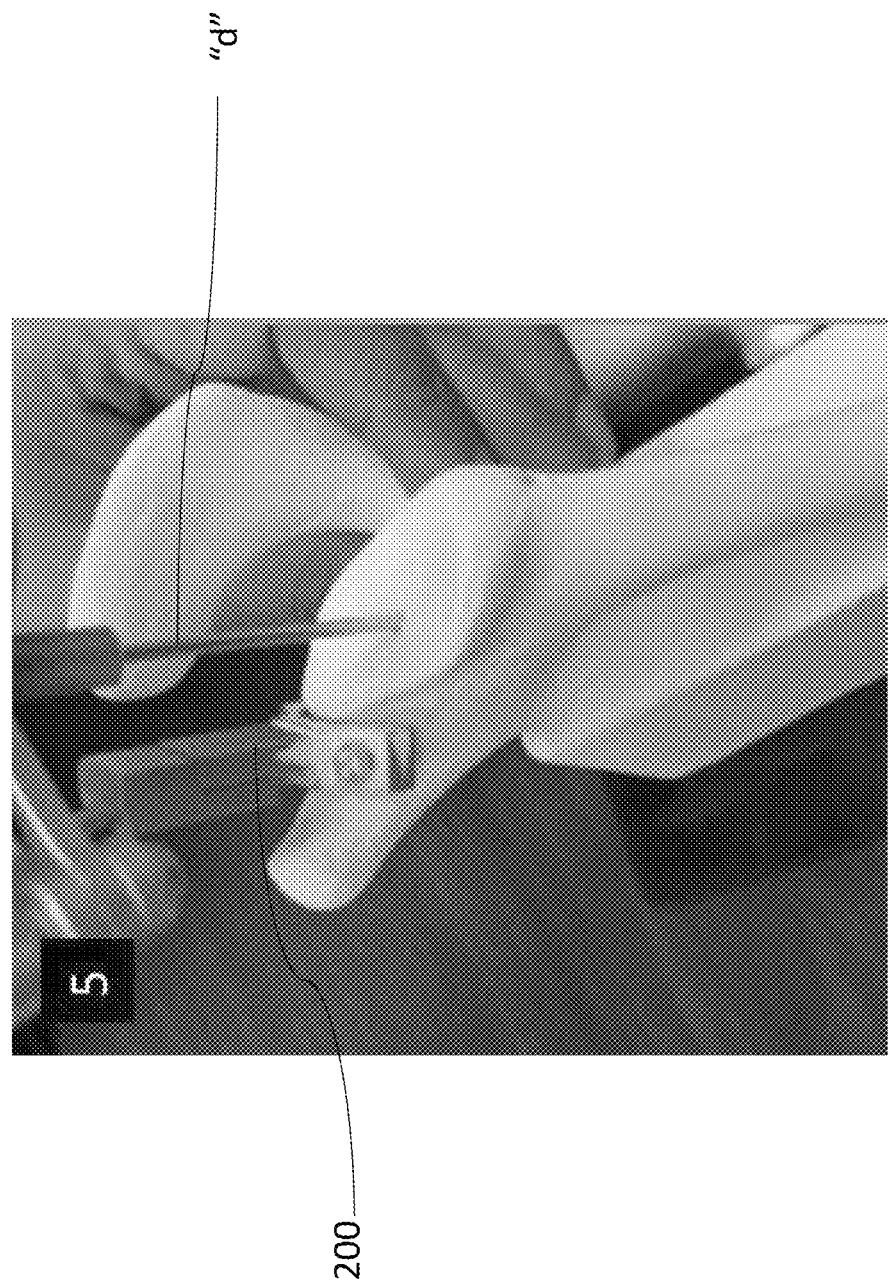

Referring now to FIG. 12, the PSI 400 is removed from the robot mount 306 of the remote robot 300 and is coupled to the bone mount 200 secured to coracoid base "b" of the shoulder. (FIG. 4). Since the bone mount 200 and the robot mount 306 of the remote robot 300 are registered, upon positioning the PSI 400 on the bone mount 200, the PSI guide 404 is aligned with the spatial target "s." Moreover, upon mounting to the bone mount 200, the PSI guide 404 is at the desired orientation relative to the glenoid bone structure "b" as effected by the adjustments provided by the robotic platform. In this position, a surgical procedure may be performed (STEP 120) including for example, and without limitation, advancing a guidewire through the PSI guide 404 and into the glenoid bone tissue "g." In illustrative embodiments, a drill may be utilized to form an opening along the glenoid scapular axis through the PSI guide 404 followed by insertion of the guidewire. In other illustrative embodiments depicted in FIGS. 13 and 14, the PSI guide tube section 406 can receive an instrument such as a drill, guidewire, reamer, etc. in the absence of the PSI guide 404. In other embodiments, a prosthesis or any other surgical devices or instruments the like may be substituted for the guidewire. Prior to insertion of the guidewire or prosthesis, confirmation of the orientation and location of the PSI guide 404 and/or the actual guidewire may be ascertained by digitizing the guidewire and comparing the digitized data to the preoperative dataset.

Figure 15:
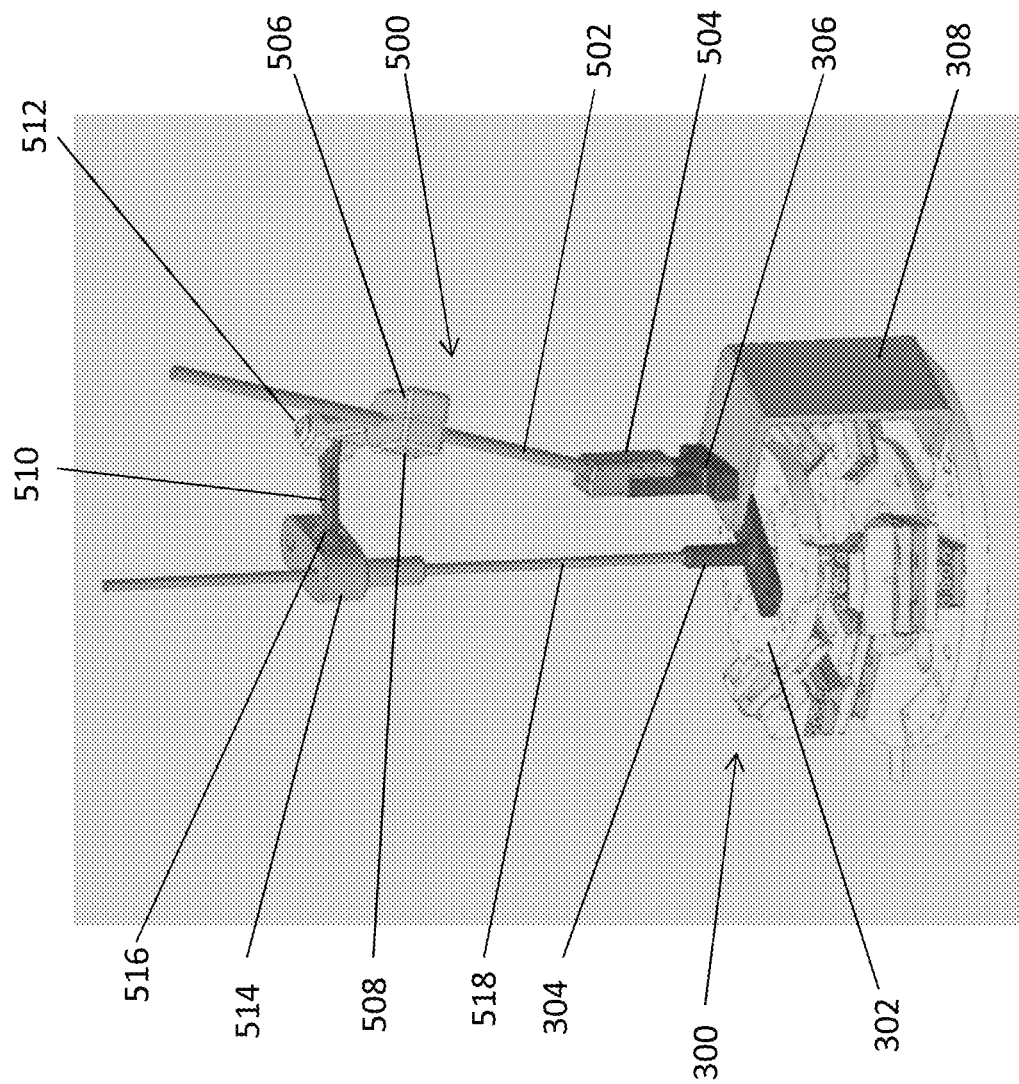
FIG. 15 illustrates another exemplative embodiment of a PSI 500 mounted to the robot bone mount of the remote robot in accordance with one or more exemplative embodiments of the present disclosure.

FIG. 15 illustrates another exemplative embodiment of a patient specific instrument (PSI) 500 mounted to the robot mount 306 of the remote robot 300. The PSI 500 may take various forms depending on the intended use of the PSI 500 such as for example, and without limitation, the PSI 400 of FIGS. 8 and 9. In illustrative embodiments, the PSI 500 includes a surgical arm 502 including a rectangular base 504 (FIG. 4) having a recessed segment which slides over the robot mount 306 of the remote robot 300 and the bone mount 200 of the on the glenoid bone structure "g" (FIG. 4). The rectangular base 504 of the surgical arm 502 and the may be correspondingly dimensioned to establish a close tolerance relationship to stabilize the surgical arm 502 relative to the bone mount 200, and thus to the coracoid base "c" and the glenoid bone structure "g." Other mechanisms for securing the surgical arm 502 to the bone mount 200 are also envisioned. Attached thereto or as a component of the surgical arm 502 is a coupler 506. The coupler 506 may be adjustably secured to the surgical arm 502 via one or more fasteners 508. An instrument arm mount 510 is coupled to the coupler 506 via an adjustable fastener 512 which permits selective movement of the arm mount 510 relative to the coupler 506. An instrument holder 514 is mounted to the arm mount 510 via a gimbal mount 516. The gimbal mount 516 enables rotational and/or translational movement of the instrument holder 514 relative to the instrument arm mount 510 and the surgical arm 502. The instrument holder 514 holds a PSI guide 518. The PSI guide 518 may be a guide wire, guide tube, cannula etc. which is utilized, for example, in conjunction with a surgical tool such as a guide wire, reamer, drill etc. to perform a surgical procedure. Although described as individual components, the surgical arm 502, the coupler 506, the arm mount 510 and the instrument holder 514 may be considered individually, or in combination, to be a terminal robot arm of a surgical robot. The surgical arm 502, instrument arm mount 510, the instrument holder 514 and/or the guide 518 may be incorporated into the composite dataset via the digitizer as described hereinabove simultaneous with, or subsequent to, the initial operative scanning processes. It is envisioned that other arrangements of the surgical arm 502, instrument arm mount 510, the instrument holder 514 and the guide 518 may be utilized and adapted to perform the surgical procedure on the glenoid bone structure "g."

The remote robot 300 is manipulated in accordance with the description of STEP 114 of the flow chart 100 whereby the guide 304 of the surgical robot 300 is aligned with the spatial target "s." In illustrative embodiments, the PSI 500 is mounted to the robot mount 306 and the PSI guide 518 of the PSI 500 is placed within the guide 304. The PSI 500 is secured via at least fasteners 508, 512 thereby aligning the PSI guide 518 of the PSI 500 with the spatial target "s." In other illustrative embodiments, the PSI 500 is secured in a loose or untightened condition to the robot mount 306 and the remote robot 300 is manipulated to align the robot guide 304 with the PSI guide 518. Thereafter, the PSI 500 is secured via at least fasteners 508, 512 thereby aligning the PSI guide 518 of the PSI 500 with the spatial target "s" as described in STEP 116 of the flow chart 100. The PSI 500 is removed from the robot mount 306 of the remote robot 300 and is coupled to the bone mount 200 secured to coracoid base "b" of the shoulder. (FIG. 4). Since the bone mount 200 and the robot mount 306 of the remote robot 300 are registered, upon positioning the PSI 500 on the bone mount 200, the PSI guide 518 is aligned with the spatial target "s." Moreover, upon mounting to the bone mount 200, the PSI guide 518 is at the desired orientation relative to the glenoid bone structure "b" as effected by the adjustments provided by the robotic platform. In this position, a surgical procedure may be performed (STEP 120) including for example, and without limitation, advancing a guidewire through the PSI guide 518 and into the glenoid bone tissue "g.". In illustrative embodiments, a drill may be utilized to form an opening along the glenoid scapular axis through the PSI guide 518 followed by insertion of the guidewire. In other embodiments, a prosthesis or any other surgical devices the like may be substituted for the guidewire. Prior to insertion of the guidewire or prosthesis, confirmation of the orientation and location of the PSI guide 518 and/or the actual guidewire may be ascertained by digitizing the guidewire and comparing the digitized data to the preoperative dataset.

Figure 16B:
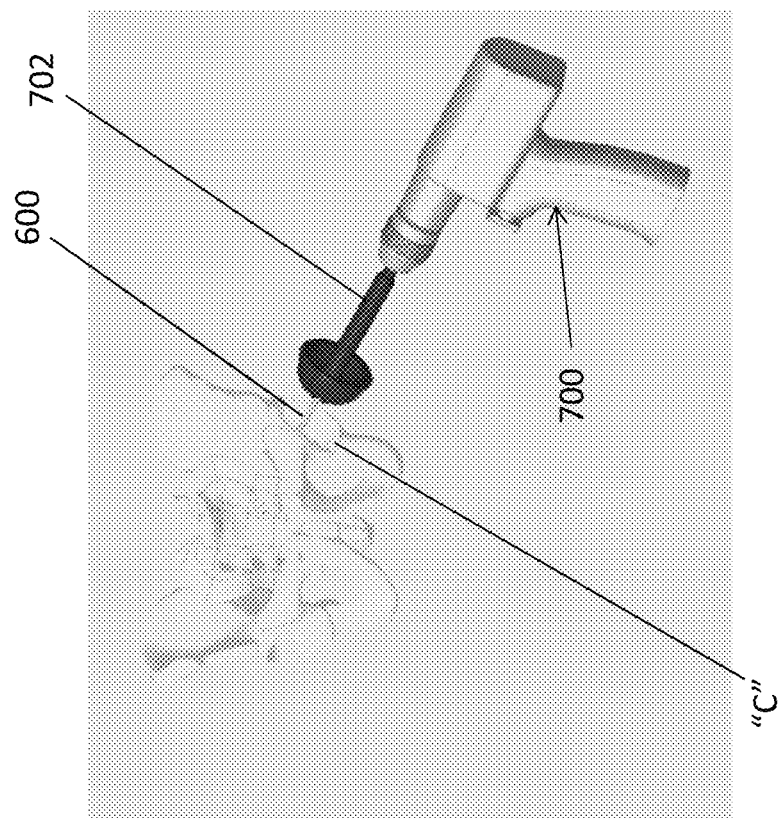
FIGS. 16A-16E illustrate an exemplative use of a PSI with the remote robot for performing a total hip arthroplasty procedure (THA) in accordance with one or more exemplative embodiments of the present disclosure.
Figure 16A:
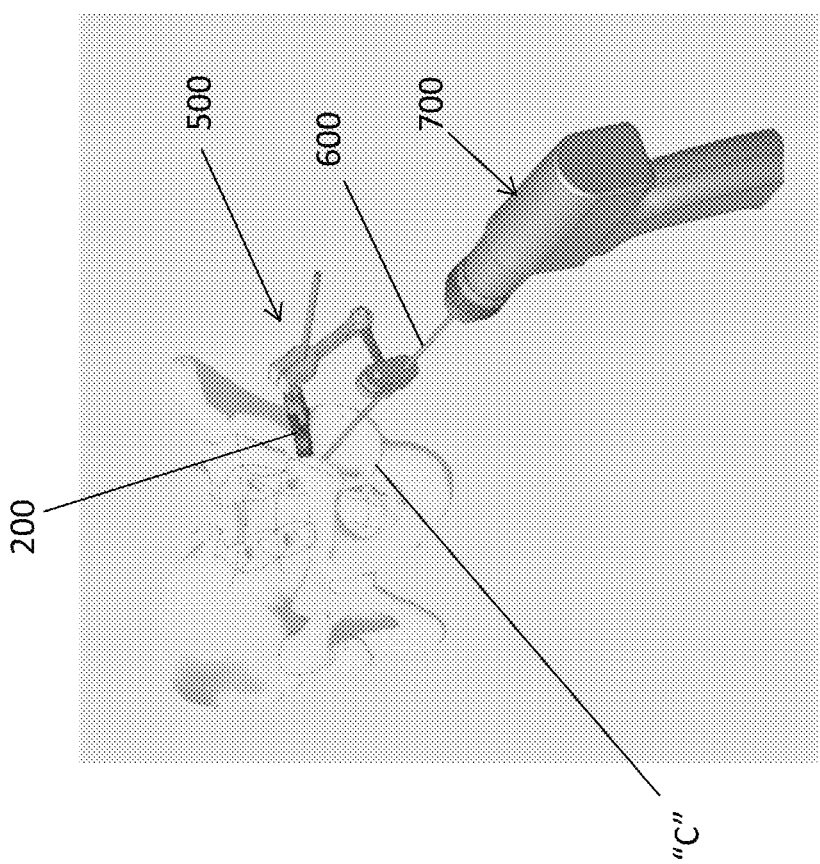
Figure 16D:
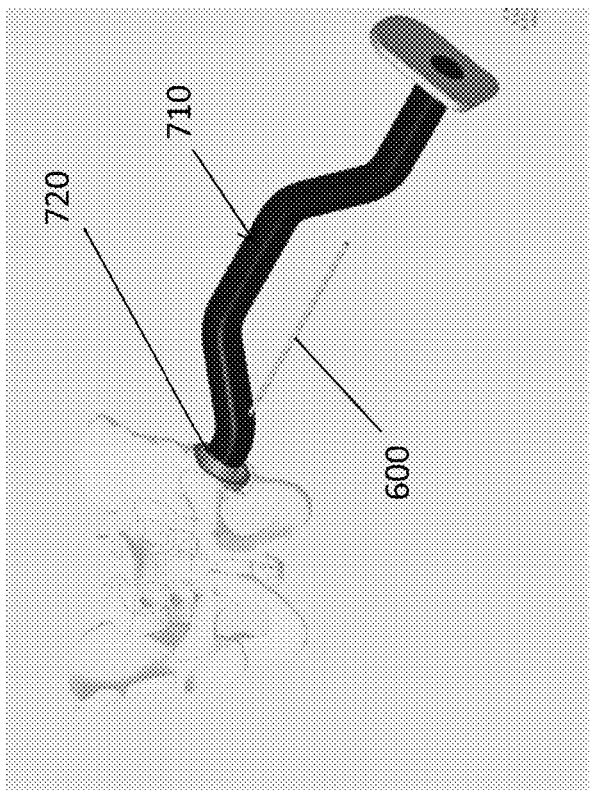
Figure 16C:
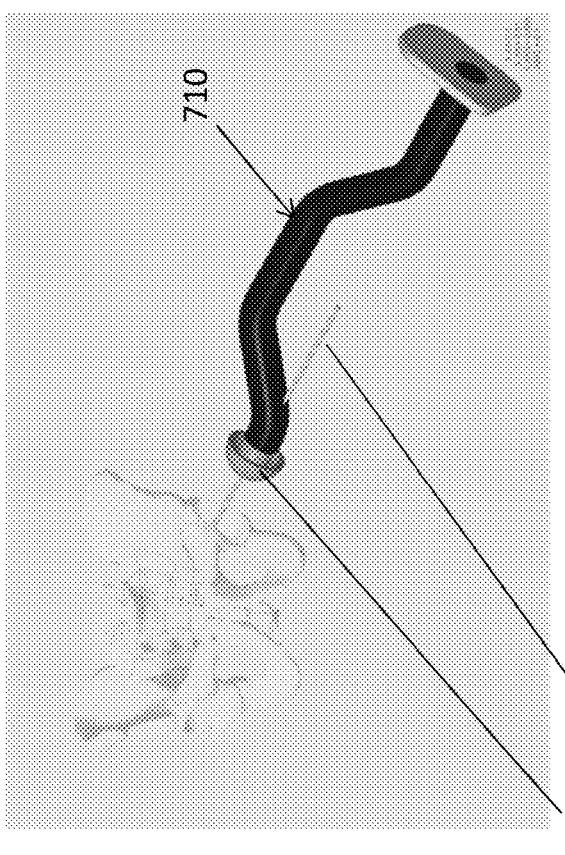
Figure 16E:
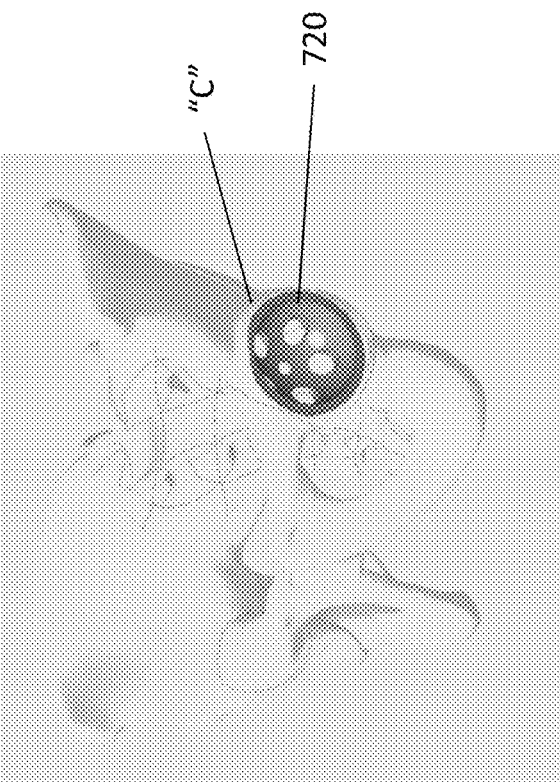

FIGS. 16A-16E illustrate an exemplative use of the patient specific instrument 500 with the remote robot remote robot 300 for a total hip arthroplasty procedure (THA). The acetabulum "c" is accessed and a bone mount 200 is positioned adjacent the socket as shown in FIG. 16A. STEPS 102-118 of flow chart 100 are performed to appropriately position the PSI 500 relative to the spatial target, i.e., the axis of the acetabulum. A guide pin 600 is positioned within the alignment component of the PSI 500 and advanced in concert with the spatial target against and/or into the bone tissue. A drill 700 may be attached to the guide pin 600 to facilitate penetration within the bone tissue. With the guide pin 600 aligned along the spatial target, the PSI 500 may be removed. As depicted in FIG. 16B, a reamer 702 is attached to the drill 700 and advanced along the guide pin 600. The reamer 702 is utilized to remove bone tissue and prepare the site for an implant. With reference to FIG. 16C, the reamer 702 is removed from the guide pin 600 and an implant insertion instrument 710 is positioned along the guide pin 600. The implant insertion instrument 710 includes an acetabular implant 720 mounted thereto. The implant insertion instrument 710 is advanced along the guide pin 600 (FIG. 16D to implant the acetabular implant 720. (FIG. 16E). The implant insertion instrument 710 and the guide pin 600 are thereafter removed.

Figure 17:
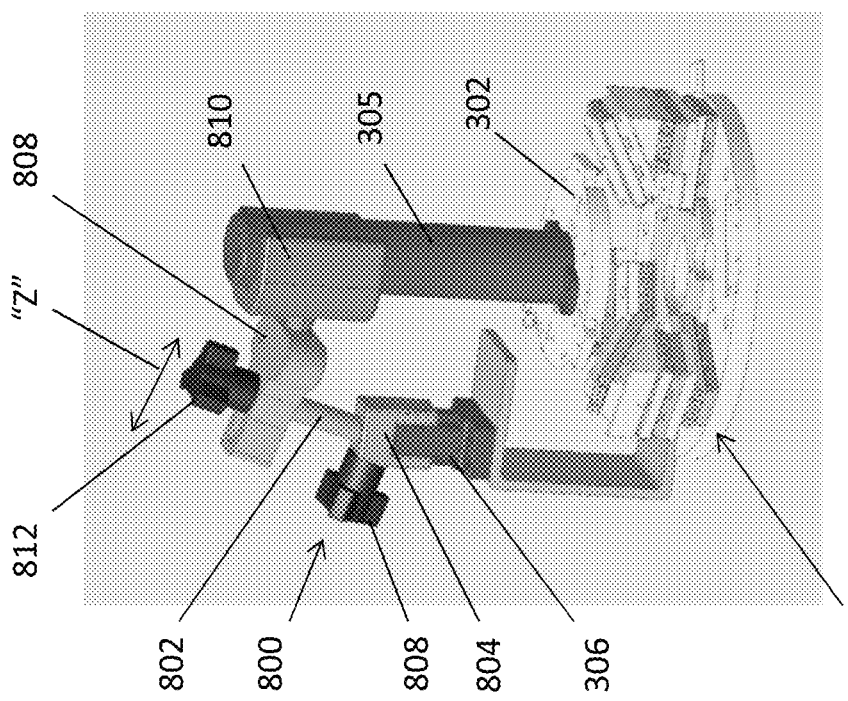
FIG. 17 is a view illustrating another embodiment of a PSI for placement of an acetabular implant in accordance with one or more exemplative embodiments of the present disclosure.

FIG. 17 illustrates another exemplative embodiment of the PSI of the present invention. The PSI 800 may be used for placement of an acetabular implant without use of a guide pin. The PSI 800 includes an arm 802 with a base 804 which is mounted to the robot mount 306. The arm 802 can articulate relative to the base 804. A fastener 806 can secure the arm 802 at a plurality of angular positions relative to the base 804. A coupler 808 is mounted to an upper portion of the arm 802. The coupler 810 has an alignment component 810. The coupler 808 can move in transverse relation relative to the arm 804 (direction arrows "z") to adjust the location of the coupler 808. A fastener 812 may secure the coupler at any desired location relative to the arm 802. In illustrative embodiments, the alignment component 810 may articulate relative to the coupler 808 via a gimbal mount or the like. In the alternative, the alignment component 810 may be fixed to the coupler 808. In this embodiment, the remote robot 300 includes a robot guide 305 which is generally cylindrical in configuration to correspond to the outer dimension of an insertion tool.

STEPS 102-116 of the flow chart 100 of FIG. 1 are repeated with the PSI 800 to align the robot guide 305 and the alignment component 810 of the PSI 800 with the spatial target.

Figure 18A:
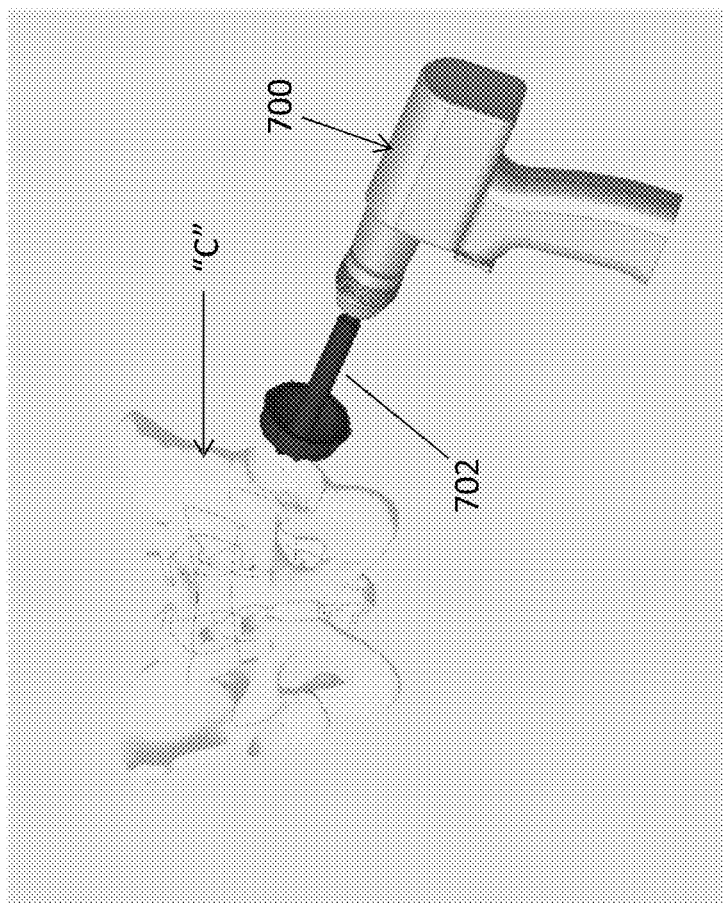
FIGS. 18A-18D are views illustrating a sequence of steps for placement of the acetabular implant with the PSI of FIG. 17 in accordance with one or more exemplative embodiments of the present disclosure.
Figure 18B:
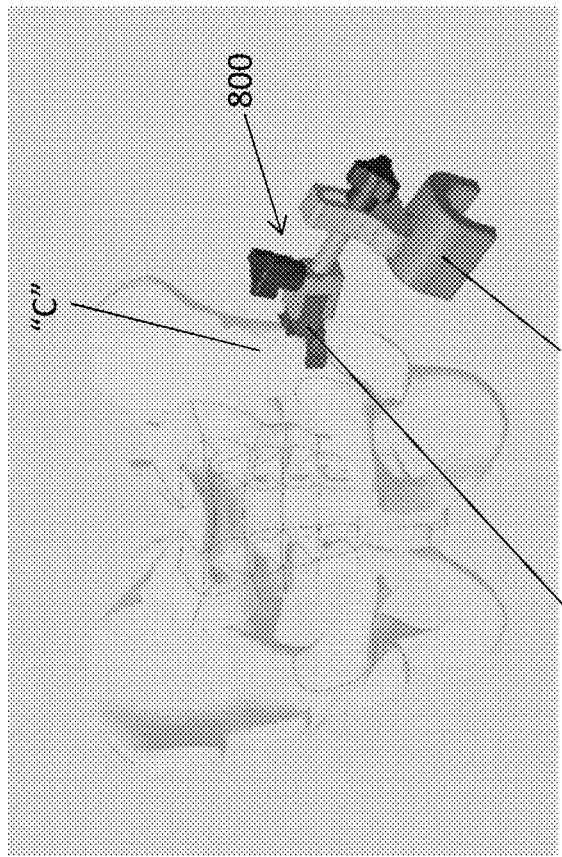
Figure 18D:
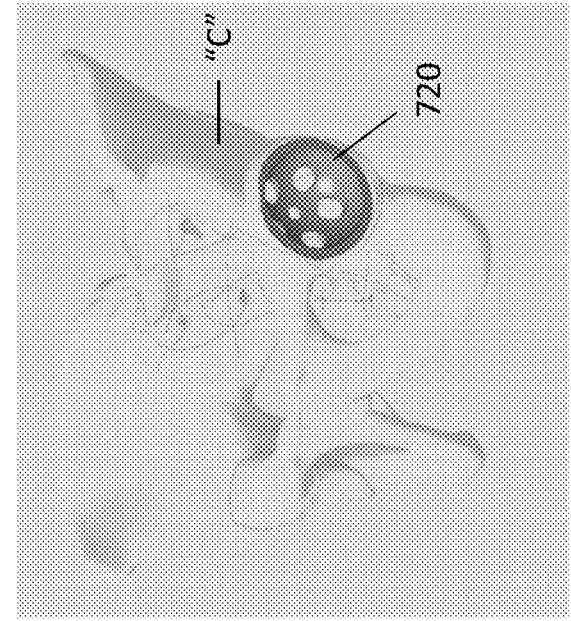
Figure 18C:
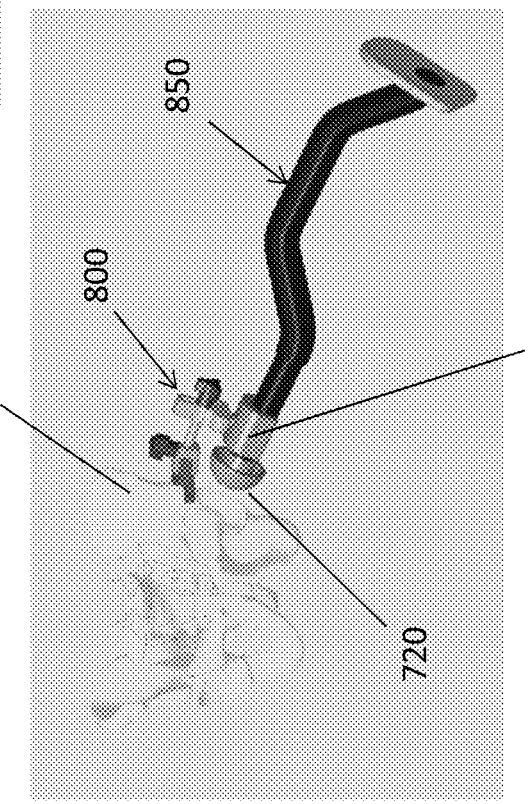

Referring now to FIGS. 18A, the acetabular is prepared with the use of a drill and reamer 702. In illustrative embodiments, the reamer 702 may be used with a guide pin as described hereinabove in connection with FIGS. 16A and 16B. In the alternative, the drill 700 and the reamer 702 may be used without a guide pin. The bone mount 200 is positioned adjacent the socket and the PSI 800 is attached to the bone mount 200 in accordance with the methodology of the flow chart 100 of FIG. 1. (FIG. 18B) With the PSI 800 mounted, the axis of the alignment component 810 is aligned with the spatial target, e.g., the acetabular joint. An insertion tool 850 including the acetabular implant 720 is positioned within the alignment component 810 of the PSI 800. The insertion tool 850 is advanced within the alignment component 810 in line with the spatial target (FIG. 18C) and the implant is positioned in the previously prepared acetabular joint "C." (FIG. 18D).

FIG. 19 illustrates another embodiment of a PSI for use in, for example, establishing a spatial target as a plane. The remote robot 300 is substantially similar to the remote robot 300 described hereinabove, including multiple platforms 302 which may articulate. Mounted to the platforms 302 is a planar base 315 and a guide connector 317 extending from the planar base 315. The guide connector 317 includes a guide leg 319 in alignment with the base 315. The connection to the planar base 315 through the guide connector 317 allows for control or rotation of PSI 900. This allows for control of 6 degrees of freedom to control a plane. A robot mount 306 is secured to a side of the robot 300 although other locations for the robot mount 306 are envisioned. The PSI 900 includes a PSI mount 902 for coupling to the robot mount 306. A PSI arm 904 is coupled to the PSI mount 902. The PSI arm 904 may pivot or angulate relative to the PSI mount 902. A PSI planar alignment member 906 is mounted to the PSI arm 904. The PSI planar alignment member 906 may reciprocally rotate in directions "K" relative to the PSI arm 904. The PSI alignment member 906 is couplable to the guide leg 319 through one or more fasteners. The PSI alignment member 906 may optionally include a parallel longitudinal alignment slot 908. The combination of movement capabilities provided via, for example, the rotating PSI arm 904 and articulation of the robot base 302 enables controlled movement for the PSI 900 along six (6) degrees of freedom of movement and relative to the robot mount 306.

The PSI 900 is used to perform a surgical procedure as described in connection with the flow process 100 of FIG. 1. However, instead of establishing the spatial target along an axis, in accordance with the use of the PSI 900, the spatial target is defined as a plane. More specifically, in STEP 104, the spatial target is defined along a plane which may correspond to a location for performing a planar cut of tissue. Once the planar spatial target is defined, the process of FIG. 1 is followed. In illustrative embodiments, the robot platforms 302 are manipulated to align the guide leg 319 and/or planar guide 315 of the remote robot 300 with the planar spatial target. Alignment of the guide leg 319 and/or the planar guide 315 also aligns the PSI planar alignment member 906 with the planar spatial target via the guide leg 319 and/or the planar guide 315. In further embodiments, alignment of the guide leg 319 and/or the planar guide 315 also aligns the longitudinal alignment slot 908 with the planar spatial target.

Once aligned, the PSI 900 may be secured in a locked condition with fasteners etc. as described hereinabove. In other embodiments, no fasteners are required and can be locked by other means such as magnetic or interlocking ridges.

Figures 20B, 20C, 20D:
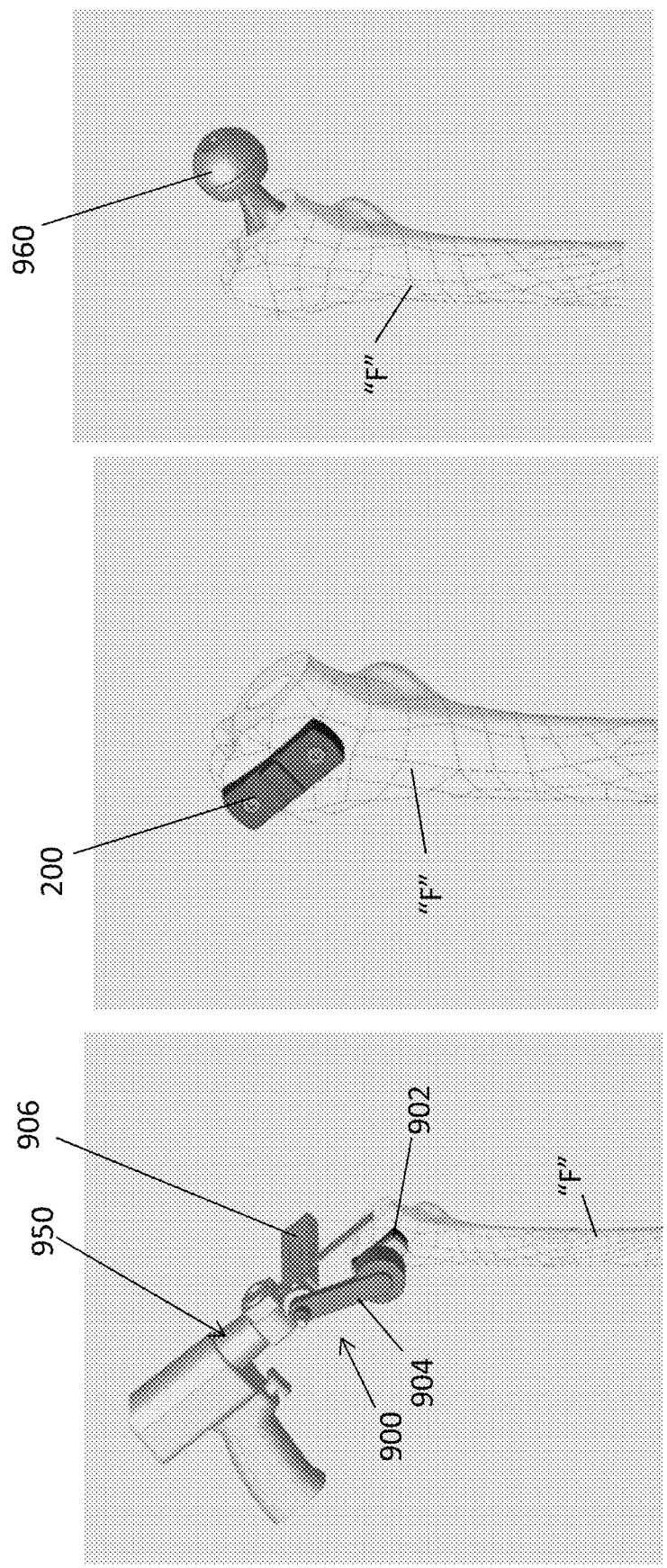

FIGS. 20A-20D illustrate use of the PSI 900 with the remote robot 300 in connection with performance of a total hip arthroplasty. The planar spatial target is identified and a bone mount 200 is secured to the femur "f." (FIG. 20A) The remote robot is manipulated to align the PSI alignment member 906 with the spatial target. The PSI 900 is mounted to the bone mount 200 and a surgical cutting tool 950 configured to form a planar cut in tissue is mounted to the PSI planar alignment member 906. (FIG. 20B). In illustrative embodiments, the planar cutting tool 950 includes a planar blade 952 which extends through, for example, the longitudinal alignment slot 908 of the alignment member 906. The planar blade 952 aligned with the planar spatial target is used to sever the upper portion of the femur adjacent the femoral head. (FIG. 20C). The PSI 900 and surgical tool 950 are removed and an implant 960 is positioned within the femoral head region. (FIG. 20D)

Figure 21A:
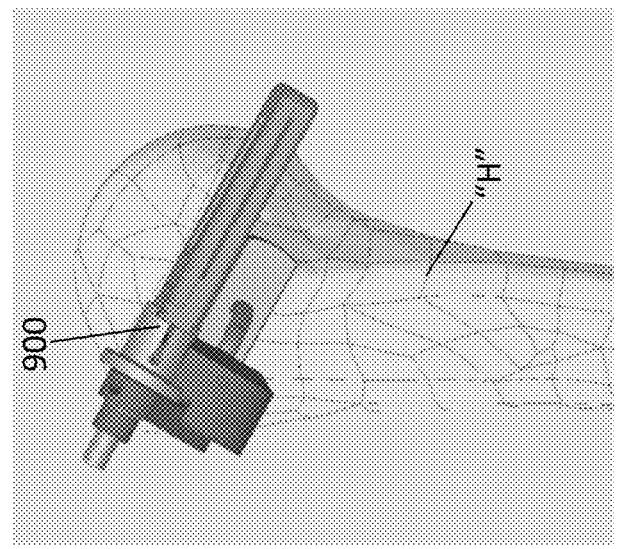
FIGS. 21A-21D illustrate the use of the PSI of FIG. 19 to form a planar cut in the humerus "h" in association with a shoulder replacement in accordance with one or more exemplative embodiments of the present disclosure.
Figure 21B:
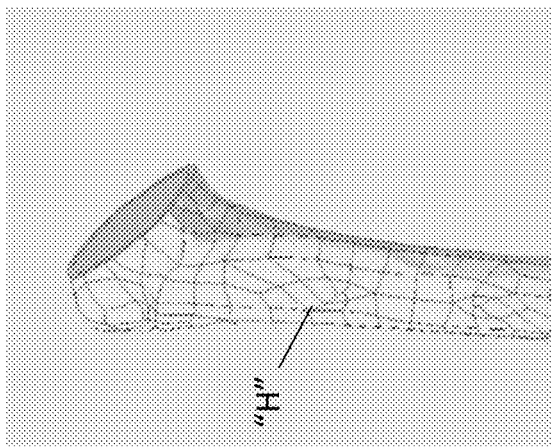
Figure 21C:
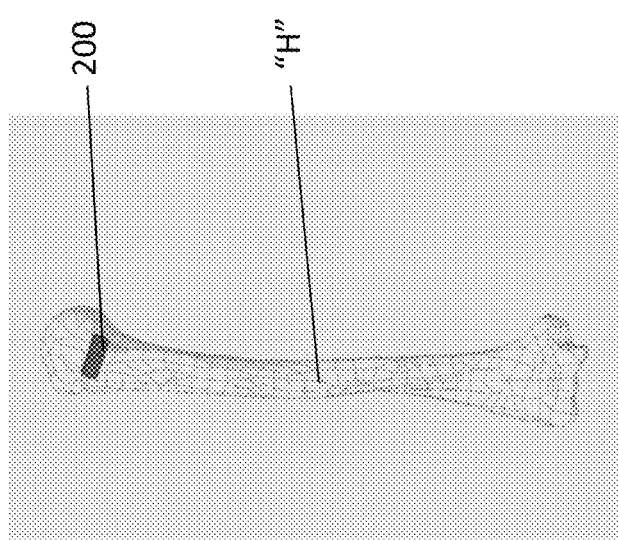
Figure 21D:
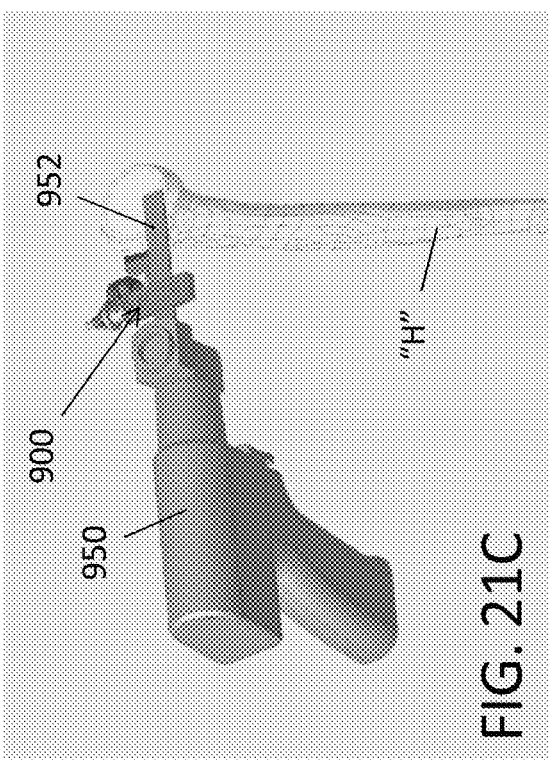

FIGS. 21A-21D illustrate the use of the PSI 900 to form a planar cut in the humerus "h", for example, in association with a shoulder arthroplasty. A bone mount 200 is mounted to the humerus. (FIG. 21A) The spatial plane is identified and translated to the remote robot 300. The PSI 900 is adjusted to correspond with the planar spatial plane. The PSI 900 is returned to the operative site and mounted to the bone mount 200 (FIG. 21B). The surgical tool 950 is used to form a planar cut along the planar spatial target guided by the PSI. (FIG. 21C). The instrument 950 and the PSI are removed (FIG. 21D) to enable, for example, insertion of an implant.

Figure 22C:
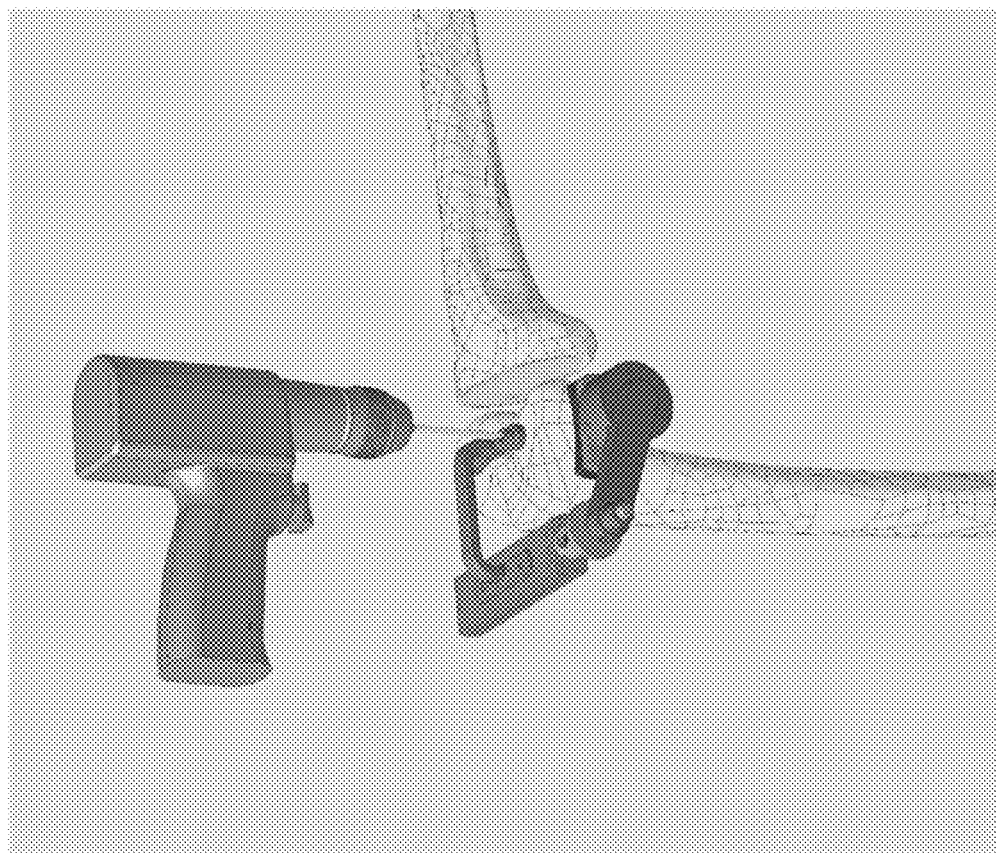

FIGS. 22A-22D illustrate the use of the PSI 900 is performing a total knee arthroplasty (TKA). The bone mount 200 is mounted at the desired location adjacent the knee joint "N" (FIG. 22A). The planar spatial target is identified and translated back to the remote robot 300 which aligns the PSI 900 with the spatial target. The PSI 900 is returned to the operative site and mounted to the bone mount 200. (FIG. 22B). The surgical cutting tool is used to cut a first planar surface "S1" along a first planar spatial target. Thereafter, in a second step the robot positions the location of an extension arm attached to the first cutting guide (FIG. 22C) to place two guide pins into the distal cut surface of the femur. These two pins control the location and rotation of a second cutting guide 975 shown in FIG. 22D to complete the preparation of the femur FIG. 22E. In illustrative embodiments, an additional guide plate 975 may be secured to the first planar surface "S1" (FIG. 22C). The additional guide plate 975 over the two guide pins placed in FIG. 22C may include a longitudinal slot 977 (FIG. 22D) for reception of the cutting blade 952 of the cutting tool 950 to cut a second planar surface "S2." (FIG. 22C) The cutting tool 950 and the additional guide plate may be removed to complete the TKA procedure. (FIG. 22D).

Figure 23:
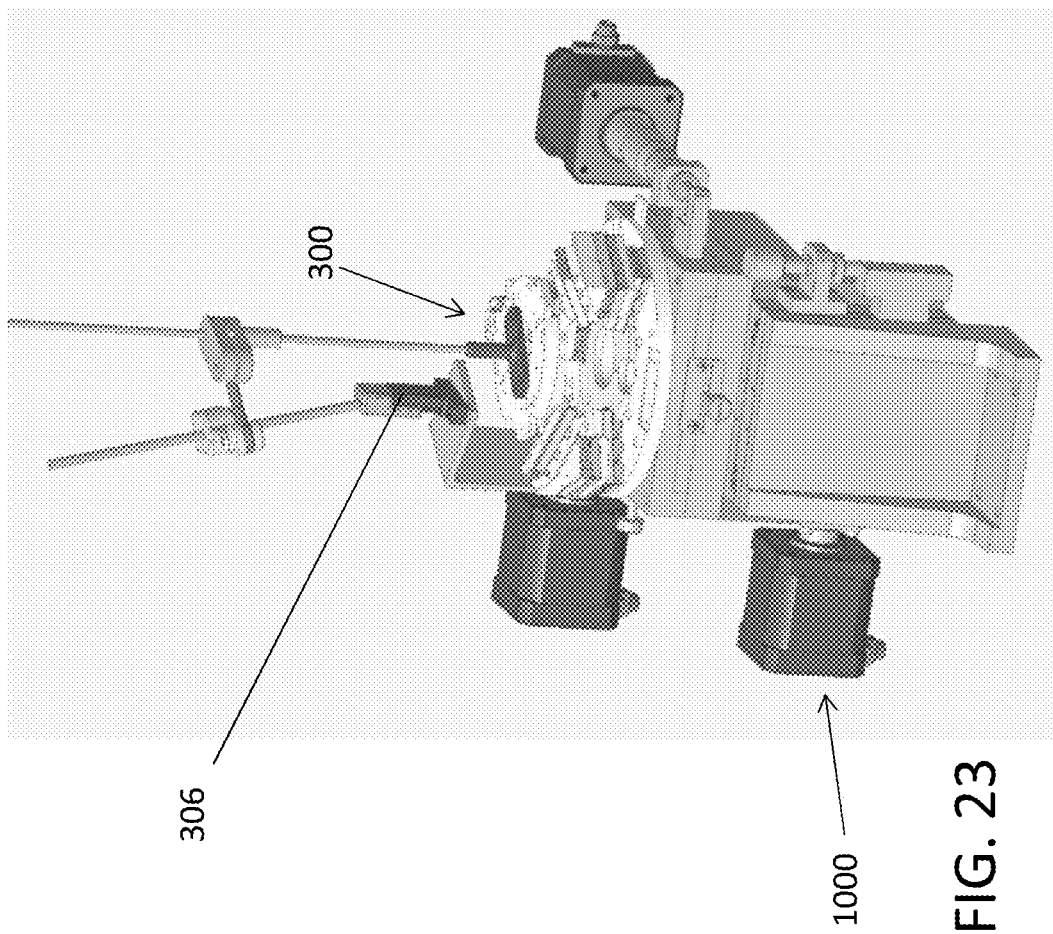
FIG. 23 is a view illustrating another alternate embodiment illustrating mounting the primary remote robot to a second macro remote robot (1000) where the robot reference bone mount is attached to the macro robot and moves the primary robot in relation to the reference bone mount in accordance with one or more exemplative embodiments of the present disclosure.
Figure 24A:
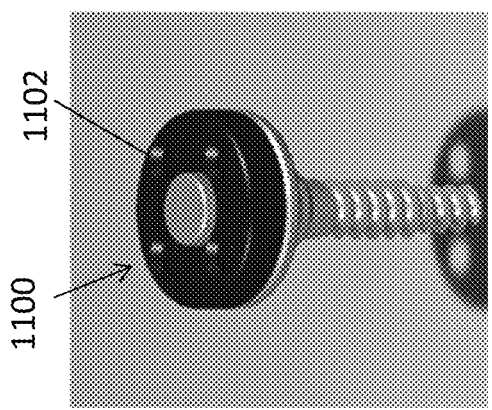
FIGS. 24A-24D are views illustrating another embodiment of a PSI for implantation of a screws into an orthopedic implant in accordance with one or more exemplative embodiments of the present disclosure.
Figure 24B:
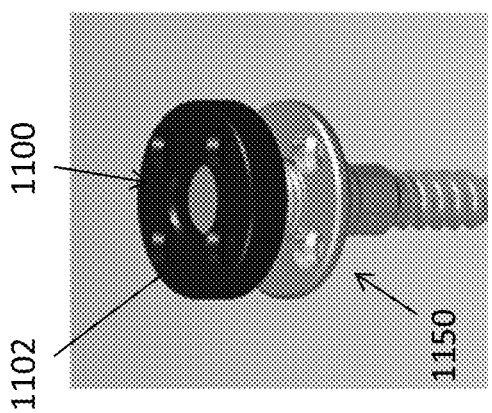
Figure 24C:
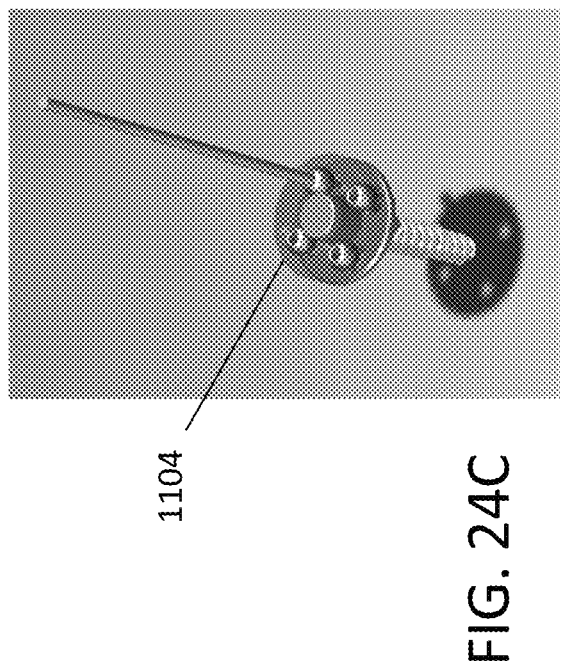
Figure 24D:
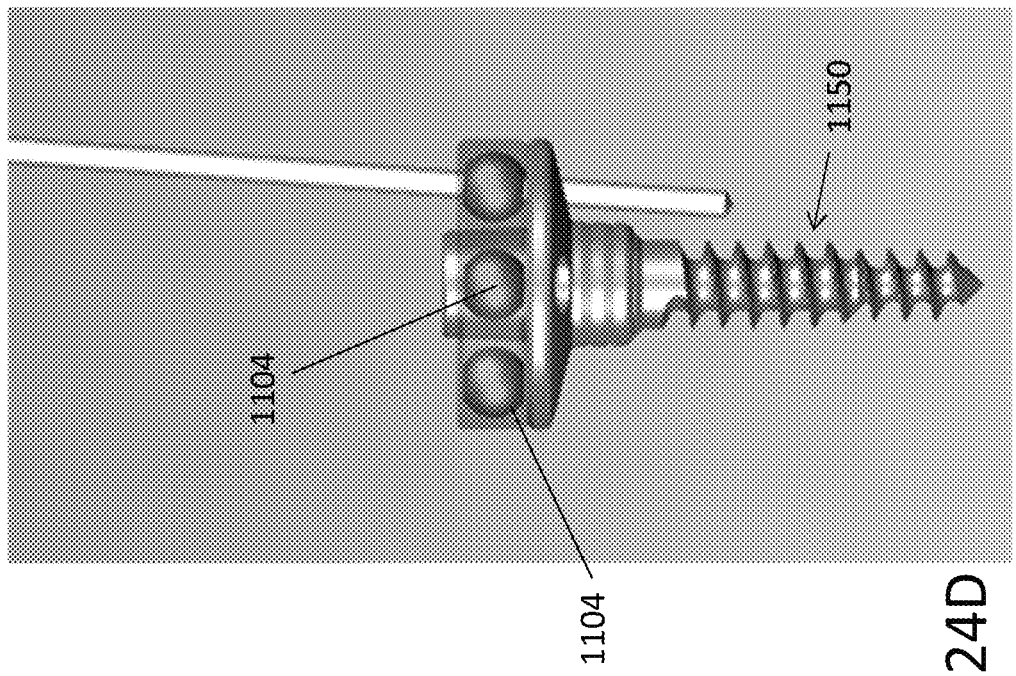

FIG. 23 is a view illustrating another alternate embodiment of the present disclosure. In accordance with this embodiment, the remote robot 300 is mounted to a second remote robot 1000. In this case the robot mount 306 is secured to the second robot. The purpose of this is to move the primary robot in relation to the robot mount 306. The second macro remote robot 1000 is configured to provide 3 axis X-Y-Z translational stage movement for in plane larger translation and rotation. This coupled with movement of the remote robot 300 provides an enhanced range and flexibility to the surgeon to accommodate vast degrees of spatial targets.

FIGS. 24A-24D illustrate another embodiment of the present disclosure. The PSI 1100 is designed for control of the orientation of screws within an implant 1150. The PSI 1100 includes one or more openings 1102 each having a cannulated spherical ball 1104. The cannulated spherical balls 1104 may rotate freely within the openings 1102. The cannulated spherical balls 1104 are configured to receive screws to facilitate securement of the implant 1150. In use, the spatial target is defined for each screw to be positioned in the head of the orthopedic implant 1150. The PSI 1100 is transferred to the remote robot and the spatial target is set for each screw. The remote robot is manipulated such that a guide of the robot adjusts the spherical ball 1104 at the desired orientation aligned with the axis of the spatial target. This process can be repeated for each cannulated ball. The PSI 1100 is returned to the operative area and mounted to the implant 1150 with the cannulated spherical balls aligned with each spatial target. Fasteners are then introduced into the cannulated spherical balls 1104 and secured to the tissue.

Thus, in accordance with the process of the present disclosure, the robotic platform is not used to perform the actual surgical procedure but is employed to arrange and manipulate, in conjunction with the composite dataset, the PSI at the desired position and orientation to coincide with the location and orientation of the spatial target. More specifically, the robotic platform provides the fine tuning and adjusting of the PSI such that when returned to the operative site the PSI is at the desired orientation to enable placement of the guidewire or other device in accordance with the corresponding to the spatial target established in the preoperative or operative dataset.

The robotic platform may be positioned at any location remote from the surgical site including within the operating room or an adjacent room or the like. The robotic platform may be any suitable platform configured to perform one or more surgical procedures. In one example, the robotic platform includes a 6 degree of freedom robot for precision motion platform to enable fine tuning of the PSI.

As noted hereinabove, it is envisioned that the process and system of the present disclosure may have other applications in the surgery including orthopedic surgery, arthroplasty, etc. and may have application in dental procedures as well. The process may have application in a manufacturing environment to enable precise robotic fine tuning and adjustments of implements used in manufacture or repair of various items. Other applications are also contemplated.

Embodiments of the present disclosure may be implemented via a distributed communications/computing network (processing platform). By way of illustration, FIG. 25 depicts a communication system 1200 that includes one or more computing devices 1204-1 through 1204-P (herein collectively referred to as computing devices 1204 with one or processors coupled to memory) configured to communicate with one another over a network 1202.

The network 1202 may include, for example, a global computer network such as the Internet, a wide area network (WAN), a local area network (LAN), a satellite network, a telephone or cable network, or various portions or combinations of these and other types of networks (including wired and/or wireless networks). As described herein, the computing devices 1204 may represent a large variety of devices including a desktop or laptop personal computer (PC), a server, a microcomputer, a workstation, a kiosk, a mainframe computer, or any other information processing device which can implement any or all of the techniques detailed in accordance with one or more embodiments of the invention. Other computing devices include a portable device such as a mobile telephone, a smart phone, tablet, computer, a client device, etc.

By way of example, in an Internet-based and/or telephony-based environment, the system is configured to enable a user, for example, a surgeon, to perform one or more steps of the methodology described herein.

Figure 25:
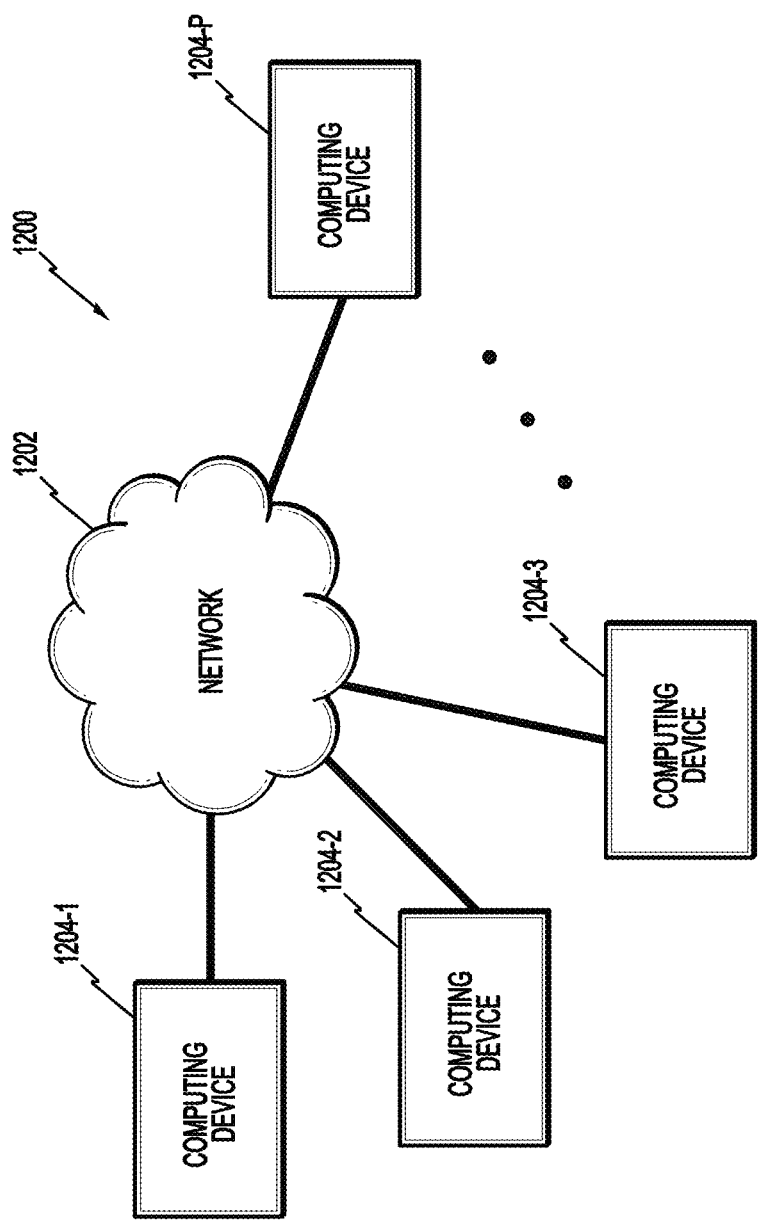
FIG. 25 depicts an exemplative communication system for implementing the methodologies in accordance with the present invention.

In one or more embodiments, the computing system environment shown in FIG. 25 employs a cloud computing platform, where "cloud" refers to a collective computing infrastructure that implements a cloud computing paradigm. Cloud-based computing platforms (also sometimes referred to as data centers) are deployed and managed by cloud service providers, who provide a computing environment for customers (tenants) to run their application programs (e.g., business applications or otherwise). The applications are typically run on one or more computing devices (i.e., host devices or hosts), and write data to and read data from one or more storage devices (e.g., hard disk drives, flash drives, etc.). The storage devices may be remote from the host devices such that they are connected via a communication network. However, some or all of the storage devices may be part of the same computing devices that implement the hosts.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method, comprising:
obtaining a digitized 3D dataset of a procedural site where a surgical procedure is to be performed, the digitized 3D dataset including a surgical reference;
identifying a spatial target in the digitized 3D dataset of the procedural site;
accessing a remote robot disposed at a remote location relative to the procedural site;
registering a replica reference associated with the remote robot to the surgical reference within the digitized 3D dataset;
coupling a patient specific instrument relative to the remote robot, the patient specific instrument having a tool associated therewith;
manipulating, with the remote robot, the tool to a replica spatial target based at least in part on the digitized 3D dataset and the replica reference, the replica spatial target corresponding to the spatial target within the procedural site;
securing the tool relative to the patient specific instrument;
removing the patient specific instrument from the remote robot and moving the patient specific instrument to the procedural site;
mounting the patient specific instrument relative to the surgical reference such that the tool is aligned with the spatial target; and
performing one or more operations with the tool;
wherein the surgical reference includes a tissue mount, the tissue mount being represented in the digitized 3D dataset;
wherein the replica reference includes a replica tissue mount, the replica tissue mount being secured relative to the remote robot; and
wherein manipulating, with the remote robot, the tool includes maneuvering at least a surgical arm of the remote robot relative to the replica tissue mount to arrange the tool at the replica spatial target.

2. The method of claim 1, wherein performing one of more operations includes utilizing a second robot at the procedural site to use the tool to perform the one or more operations.

3. The method of claim 1, wherein the tool is a surgical tool.

4. The method of claim 3, including:
imaging the surgical tool within the procedural site to obtain a first 3D dataset of the surgical tool representative of at least one of location and orientation thereof to define the spatial target;
obtaining a second 3D dataset of at least tissue adjacent the procedural site; and
registering the second 3D dataset with the first 3D dataset.

* * * * *